US010675053B2

(12) United States Patent
Haack et al.

(10) Patent No.: US 10,675,053 B2
(45) Date of Patent: *Jun. 9, 2020

(54) ENDOSCOPIC SNARE DEVICE

(71) Applicant: UNITED STATES ENDOSCOPY GROUP, INC., Mentor, OH (US)

(72) Inventors: Scott Haack, Chardon, OH (US); Cindy Ranallo, Eastlake, OH (US); Craig Moore, Moreland Hills, OH (US); Alexis Uspenski, Rock Creek, OH (US); Steven Torer, Willoughby, OH (US); Raphael Still, Richmond Heights, OH (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 69 days.

This patent is subject to a terminal disclaimer.

(21) Appl. No.: 15/401,545

(22) Filed: Jan. 9, 2017

(65) Prior Publication Data
US 2017/0215910 A1 Aug. 3, 2017

Related U.S. Application Data

(63) Continuation of application No. 14/565,024, filed on Dec. 9, 2015, now Pat. No. 9,572,591, which is a
(Continued)

(51) Int. Cl.
*A61B 17/3205* (2006.01)
*A61B 17/221* (2006.01)
(Continued)

(52) U.S. Cl.
CPC .... *A61B 17/32056* (2013.01); *A61B 1/00133* (2013.01); *A61B 17/221* (2013.01); *A61B 2017/00269* (2013.01)

(58) Field of Classification Search
CPC . A61B 17/32056; A61B 17/221; A61B 17/32; A61B 17/320016;
(Continued)

(56) References Cited

U.S. PATENT DOCUMENTS

| 2,197,921 A | 4/1940 | Brown |
| 2,626,447 A | 1/1953 | Hunt |

(Continued)

FOREIGN PATENT DOCUMENTS

| DE | 19938902 A1 | 4/2000 |
| EP | 0446020 A1 | 9/1991 |

(Continued)

OTHER PUBLICATIONS

Response to Office Action from U.S. Appl. No. 14/016,906 dated Aug. 10, 2017.
(Continued)

*Primary Examiner* — Ryan J. Severson
*Assistant Examiner* — Mohamed G Gabr
(74) *Attorney, Agent, or Firm* — Calfee, Halter & Griswold LLP

(57) ABSTRACT

A tissue removal tool for use with an endoscope. The tool includes a loop formed by a piece of wire. The loop is movable between an open position and a closed position. The shape of the loop is defined in the open position by a proximal portion and a distal portion. The piece of wire may have a cross-sectional height in the proximal portion unequal to a cross-sectional height in the distal portion.

18 Claims, 25 Drawing Sheets

Related U.S. Application Data continuation-in-part of application No. 14/016,906, filed on Sep. 3, 2013, now Pat. No. 9,872,700.

(51) Int. Cl.
*A61B 17/00* (2006.01)
*A61B 1/00* (2006.01)

(58) Field of Classification Search
CPC .. A61B 2017/00269; A61B 2017/2212; A61B 2017/00358; A61B 2017/320064; A61B 2017/003; A61B 2017/00353; A61B 2018/11407; A61B 2018/141; A61B 2018/00601; A61B 18/1492
See application file for complete search history.

(56) References Cited

U.S. PATENT DOCUMENTS

| | | |
|---|---|---|
| 3,805,791 A | 4/1974 | Seuberth et al. |
| 4,083,706 A | 4/1978 | Wiley |
| 4,146,019 A | 3/1979 | Bass et al. |
| 4,200,104 A | 4/1980 | Harris |
| 4,202,338 A | 5/1980 | Bitrolf |
| 4,256,113 A | 3/1981 | Chamness |
| 4,311,143 A | 1/1982 | Komiya |
| 4,493,320 A | 1/1985 | Treat |
| 4,905,691 A | 3/1990 | Rydell |
| 4,966,589 A | 10/1990 | Kaufman |
| 5,009,642 A | 4/1991 | Sahi |
| 5,057,114 A | 10/1991 | Wittich et al. |
| 5,059,199 A | 10/1991 | Okada et al. |
| 5,078,716 A | 1/1992 | Doll |
| 5,084,054 A | 1/1992 | Bencini et al. |
| 5,098,441 A | 3/1992 | Wechler |
| 5,122,147 A | 6/1992 | Sewell, Jr. |
| 5,123,906 A | 6/1992 | Kelman |
| 5,147,371 A | 9/1992 | Washington |
| 5,156,590 A | 10/1992 | Vilmar |
| 5,171,233 A | 12/1992 | Amplatz et al. |
| 5,190,542 A | 3/1993 | Nakao |
| 5,192,280 A | 3/1993 | Parins |
| 5,192,286 A | 3/1993 | Phan et al. |
| 5,201,740 A | 4/1993 | Nakao et al. |
| 5,207,686 A | 5/1993 | Dolgin |
| 5,279,548 A | 1/1994 | Essig et al. |
| 5,336,227 A | 8/1994 | Nakao et al. |
| 5,354,303 A | 10/1994 | Spaeth et al. |
| 5,373,854 A | 12/1994 | Kolozsi |
| 5,374,273 A | 12/1994 | Nakao et al. |
| 5,376,094 A | 12/1994 | Kline |
| 5,417,697 A | 5/1995 | Wilk et al. |
| 5,423,830 A | 6/1995 | Schneebaum et al. |
| 5,441,503 A | 8/1995 | Considine et al. |
| 5,449,372 A | 9/1995 | Schmaltz et al. |
| 5,480,404 A | 1/1996 | Kammerer et al. |
| 5,496,330 A | 3/1996 | Bates et al. |
| 5,501,692 A | 3/1996 | Riza |
| 5,536,248 A | 7/1996 | Weaver et al. |
| 5,542,948 A | 8/1996 | Weaver et al. |
| 5,599,299 A | 2/1997 | Weaver et al. |
| 5,599,300 A | 2/1997 | Weaver et al. |
| 5,643,283 A | 7/1997 | Younker |
| 5,666,970 A | 9/1997 | Smith |
| 5,741,271 A | 4/1998 | Nakao et al. |
| 5,759,187 A | 6/1998 | Nakao et al. |
| 5,779,686 A | 7/1998 | Sato et al. |
| 5,782,840 A | 7/1998 | Nakao et al. |
| 5,785,689 A | 7/1998 | de Toledo |
| 5,788,681 A | 8/1998 | Weaver et al. |
| 5,810,776 A | 9/1998 | Bacich et al. |
| 5,843,028 A | 12/1998 | Weaver et al. |
| 5,843,051 A | 12/1998 | Adams et al. |
| 5,846,248 A | 12/1998 | Chu et al. |
| 5,860,987 A | 1/1999 | Ratcliff et al. |
| 5,906,594 A | 5/1999 | Scarfone et al. |
| 5,906,621 A | 5/1999 | Secrest et al. |
| 5,947,979 A | 9/1999 | Duchi et al. |
| 5,961,526 A | 10/1999 | Chu et al. |
| 5,964,740 A | 10/1999 | Ouchi et al. |
| 5,971,994 A | 10/1999 | Fritzsch |
| 5,971,995 A | 10/1999 | Rousseau |
| 5,976,073 A | 11/1999 | Ouchi |
| 5,989,264 A | 11/1999 | Wright |
| 5,997,547 A | 12/1999 | Nakao et al. |
| 6,007,546 A | 12/1999 | Snow et al. |
| 6,010,512 A | 1/2000 | Chu et al. |
| 6,015,391 A | 1/2000 | Rishton et al. |
| 6,015,415 A | 1/2000 | Avellanet |
| 6,050,995 A | 4/2000 | Durgin |
| 6,068,603 A | 5/2000 | Suzuki |
| 6,093,195 A | 7/2000 | Duchi |
| 6,123,665 A | 9/2000 | Kawano |
| 6,142,956 A | 11/2000 | Kortenbach et al. |
| 6,171,315 B1 | 1/2001 | Chu et al. |
| 6,174,291 B1 | 1/2001 | McMahon et al. |
| 6,183,482 B1 | 2/2001 | Bates et al. |
| 6,190,353 B1 | 2/2001 | Makower et al. |
| 6,193,672 B1 | 2/2001 | Clement |
| 6,210,416 B1 | 4/2001 | Chu et al. |
| 6,235,026 B1 | 5/2001 | Smith |
| 6,245,078 B1 | 6/2001 | Ouchi |
| 6,264,664 B1 | 7/2001 | Avellanet |
| 6,299,612 B1 | 10/2001 | Ouchi |
| 6,315,782 B1 | 11/2001 | Chu et al. |
| 6,319,260 B1 | 11/2001 | Yamamoto |
| 6,352,503 B1 | 3/2002 | Matsui et al. |
| 6,375,661 B2 | 4/2002 | Chu et al. |
| 6,383,194 B1 | 5/2002 | Pothula |
| 6,383,198 B1 | 5/2002 | Hamilton |
| 6,407,333 B1 | 6/2002 | Schroen |
| 6,409,733 B1 | 6/2002 | Conlon et al. |
| 6,440,138 B1 | 8/2002 | Reiley et al. |
| 6,458,074 B1 | 10/2002 | Matsui et al. |
| 6,500,182 B2 | 12/2002 | Foster |
| 6,527,753 B2 | 3/2003 | Sekine et al. |
| 6,527,781 B2 | 3/2003 | Bates et al. |
| 6,602,262 B2 | 8/2003 | Griego et al. |
| 6,616,654 B2 | 9/2003 | Mclennauer |
| 6,616,659 B1 | 9/2003 | de la Torre et al. |
| 6,669,716 B1 | 12/2003 | Gilson et al. |
| 6,730,097 B2 | 5/2004 | Dennis |
| 6,743,228 B2 | 6/2004 | Lee et al. |
| 6,770,066 B1 | 8/2004 | Weaver et al. |
| 6,773,432 B1 | 8/2004 | Clayman et al. |
| 6,827,710 B1 | 12/2004 | Money et al. |
| 6,945,956 B2 | 9/2005 | Waldhauser et al. |
| 7,001,354 B2 | 2/2006 | Suzuki et al. |
| 7,037,291 B2 | 5/2006 | Lee et al. |
| 7,037,307 B2 | 5/2006 | Dennis |
| 7,041,116 B2 | 5/2006 | Goto et al. |
| 7,044,947 B2 | 5/2006 | de la Torre et al. |
| 7,104,990 B2 | 9/2006 | Jenkins et al. |
| 7,122,003 B2 | 10/2006 | Nakao |
| 7,147,635 B2 | 12/2006 | Ciarrocca |
| 7,270,663 B2 | 9/2007 | Nakao |
| 7,387,632 B2 | 6/2008 | Ouchi |
| 7,547,310 B2 | 6/2009 | Whitfield |
| 7,575,585 B2 | 8/2009 | Goto et al. |
| 7,632,294 B2 | 12/2009 | Milbodker et al. |
| 7,691,110 B2 | 4/2010 | Secrest et al. |
| 7,704,249 B2 | 4/2010 | Woloszko et al. |
| 7,758,591 B2 | 7/2010 | Griego et al. |
| 7,785,250 B2 | 8/2010 | Nakao |
| 7,951,073 B2 | 5/2011 | Freed |
| 7,972,265 B1 | 7/2011 | Chin et al. |
| 8,066,689 B2 | 11/2011 | Mitelberg et al. |
| 8,070,756 B2 | 12/2011 | Secrest |
| 8,075,572 B2 | 12/2011 | Stefanchik et al. |
| 8,100,905 B2 | 1/2012 | Weitzner |
| 8,114,099 B2 | 2/2012 | Shipp |
| 8,128,592 B2 | 3/2012 | Mitelberg et al. |
| 8,167,893 B2 | 5/2012 | Motosugi |
| 8,187,266 B2 | 5/2012 | Dickens et al. |

(56) References Cited

U.S. PATENT DOCUMENTS

| | | |
|---|---|---|
| 8,216,272 B2 | 7/2012 | Shipp |
| 8,241,210 B2 | 8/2012 | Lunsford et al. |
| 8,267,933 B2 | 9/2012 | Hamou |
| 8,282,658 B2 | 10/2012 | Knapp et al. |
| 8,298,243 B2 | 10/2012 | Carlton et al. |
| 8,317,771 B2 | 11/2012 | Mitelberg et al. |
| 8,328,803 B2 | 12/2012 | Regadas |
| 8,343,168 B2 | 1/2013 | Kaye et al. |
| 8,357,148 B2 | 1/2013 | Boulais et al. |
| 8,366,612 B2 | 2/2013 | Rosenthal |
| 8,372,066 B2 | 2/2013 | Manwaring et al. |
| 8,388,630 B2 | 3/2013 | Teague et al. |
| 8,591,521 B2 | 11/2013 | Cherry et al. |
| 9,486,188 B2 | 11/2016 | Secrest et al. |
| 9,572,591 B2 * | 2/2017 | Haack ................ A61B 17/221 |
| 9,872,700 B2 * | 1/2018 | Haack ............. A61B 17/32056 |
| 2002/0049423 A1 | 4/2002 | Howell et al. |
| 2002/0091394 A1 | 7/2002 | Reynolds et al. |
| 2002/0151889 A1 | 10/2002 | Swanson et al. |
| 2003/0139750 A1 * | 7/2003 | Shinozuka .......... A61B 17/221 |
| | | 606/113 |
| 2003/0195470 A1 | 10/2003 | Ponzi |
| 2003/0195492 A1 | 10/2003 | Gobron et al. |
| 2003/0216753 A1 | 11/2003 | Nishtala et al. |
| 2003/0236519 A1 | 12/2003 | Kear |
| 2004/0059352 A1 | 3/2004 | Burbank et al. |
| 2004/0092953 A1 | 5/2004 | Salameh |
| 2004/0158127 A1 | 8/2004 | Okada |
| 2005/0085808 A1 | 4/2005 | Nakao |
| 2005/0107668 A1 | 5/2005 | Smith |
| 2005/0267489 A1 * | 12/2005 | Secrest ................. A61B 17/22 |
| | | 606/113 |
| 2005/0267490 A1 | 12/2005 | Secrest et al. |
| 2006/0009759 A1 | 1/2006 | Christian et al. |
| 2006/0058776 A1 | 3/2006 | Bilsbury |
| 2006/0235433 A1 | 10/2006 | Secrest |
| 2006/0264977 A1 * | 11/2006 | Dana ................ A61B 17/0057 |
| | | 606/148 |
| 2007/0016225 A1 | 1/2007 | Nakao |
| 2007/0250070 A1 * | 10/2007 | Nobis ............. A61B 17/32056 |
| | | 606/113 |
| 2007/0288035 A1 | 12/2007 | Okada |
| 2008/0045945 A1 | 2/2008 | Hamou |
| 2008/0183184 A1 | 7/2008 | Kaye et al. |
| 2008/0306336 A1 | 12/2008 | Kaye |
| 2009/0043317 A1 | 2/2009 | Cavanaugh et al. |
| 2009/0112244 A1 | 4/2009 | Freudenthal |
| 2010/0036375 A1 | 2/2010 | Regadas |
| 2010/0268206 A1 | 10/2010 | Manwaring et al. |
| 2010/0268216 A1 | 10/2010 | Manwaring |
| 2011/0106077 A1 * | 5/2011 | Yanuma ........... A61B 17/32056 |
| | | 606/45 |
| 2011/0106107 A1 | 5/2011 | Binmoeller et al. |
| 2012/0004666 A1 | 1/2012 | Cowley et al. |
| 2012/0046667 A1 | 2/2012 | Cherry |
| 2012/0172662 A1 | 7/2012 | Kappel et al. |
| 2012/0172864 A1 | 7/2012 | Farin et al. |
| 2012/0184967 A1 | 7/2012 | Saleh |
| 2012/0283723 A1 | 11/2012 | Jenkins et al. |
| 2013/0018384 A1 | 1/2013 | Kappel et al. |
| 2013/0018385 A1 * | 1/2013 | Keene ............. A61B 17/32056 |
| | | 606/113 |
| 2014/0276810 A1 | 9/2014 | Raybin |
| 2014/0276911 A1 | 9/2014 | Smith et al. |
| 2015/0105789 A1 | 4/2015 | Raybin et al. |
| 2015/0157345 A1 | 6/2015 | Haack et al. |
| 2016/0242804 A1 | 8/2016 | Fleury |
| 2017/0007277 A1 | 1/2017 | Drapeau |
| 2017/0049471 A1 | 2/2017 | Gaffney |
| 2017/0231647 A1 | 8/2017 | Saunders |
| 2018/0028220 A1 | 2/2018 | Smith et al. |

FOREIGN PATENT DOCUMENTS

| | | |
|---|---|---|
| EP | 463363 A2 | 1/1992 |
| EP | 758551 A1 | 2/1997 |
| EP | 1180349 A1 | 2/2002 |
| EP | 1870015 A1 | 12/2007 |
| JP | 3-54652 | 5/1991 |
| JP | 5-091686 | 4/1993 |
| JP | 3250621 | 8/1993 |
| JP | 10-071166 | 3/1998 |
| JP | 10-174688 | 6/1998 |
| JP | 11-047154 | 2/1999 |
| JP | 11-226024 | 8/1999 |
| JP | 2000-175930 | 6/2000 |
| JP | 2000-210295 | 8/2000 |
| JP | 2000-316868 | 11/2000 |
| JP | 2000-342600 | 12/2000 |
| JP | 2003-052707 | 2/2003 |
| JP | 2003-511140 | 3/2003 |
| JP | 2007-534451 | 11/2007 |
| WO | 93/015671 A1 | 8/1993 |
| WO | 99/42041 A1 | 8/1999 |
| WO | 99/51159 A1 | 10/1999 |
| WO | 02/094082 A2 | 11/2002 |
| WO | 03/105674 A2 | 12/2003 |
| WO | 05/115116 A2 | 12/2005 |
| WO | 2006112231 A1 | 10/2006 |
| WO | 2007000452 A2 | 1/2007 |
| WO | 08/094931 A2 | 8/2008 |
| WO | 08/154406 A1 | 12/2008 |

OTHER PUBLICATIONS

Notice of Allowance from U.S. Appl. No. 14/016,906 dated Sep. 27, 2017.
Office Action from U.S. Appl. No. 14/565,024 dated Jul. 5, 2016.
Amendment from U.S. Appl. No. 14/565,024 dated Jul. 28, 2016.
Notice of Allowance from U.S. Appl. No. 14/565,024 dated Aug. 30, 2016.
Advisory Action from U.S. Appl. No. 14/565,024 dated Apr. 14, 2016.
Supplemental European Search Report from European Application No. 02729222.6 dated Aug. 20, 2009.
Response from European Application No. 02729222.6 dated Nov. 17, 2009.
Office Action from European Application No. 0279222.6 dated Sep. 23, 2010.
Response from European Application No. 02729222.6 dated Jan. 28, 2011.
Office Action from European Application No. 02729222.6 dated Sep. 7, 2011.
Response from European Application No. 02729222.6 dated Jan. 10, 2012.
Search Report from European Application No. 05757183.8 dated Oct. 4, 2012.
Office Action from European Application No. 05757183.8 dated Feb. 11, 2013.
Response from European Application No. 05757183.8 dated Aug. 19, 2013.
Search Report from European Application No. 05755966.8 dated Jun. 5, 2012.
Office Action from European Application No. 05755966.8 dated Sep. 27, 2012.
Response from European Application No. 05755966.8 dated Apr. 5, 2013.
Search Report from European Application No. 06112733.8 dated Jan. 12, 2007.
Response from European Application No. 06112733.8 dated Jan. 7, 2009.
Office Action from European Application No. 06112733.8 dated Feb. 19, 2009.
Search Report from European Application No. 12162767.3 dated Dec. 23, 2015.

(56) References Cited

OTHER PUBLICATIONS

Extended Search Report from European Application No. 14841802.3 dated Jan. 30, 2017.
Office Action from Japanese Application No. 2007-511105 dated Sep. 3, 2009.
Response from Japanese Application No. 2007-511105 dated Mar. 5, 2010 along with English translation of claims and relevant portion of remarks made in Amendment.
Office Action from Japanese Application No. 2007-515282 dated Jan. 7, 2011.
Response from Japanese Application No. 2007-515282 dated Apr. 7, 2011 along with English translation of claims and relevant portion of remarks made in Amendment.
Office Action from Japanese Application No. 2007-515282 dated Jul. 27, 2011.
Response from Japanese Application No. 2007-515282 dated Mar. 5, 2012 along with relevant portion of remarks made in Amendment.
Office Action from Japanese Application No. 2009-548397 dated Sep. 28, 2012.
Response from Japanese Application No. 2009-548397 dated Mar. 28, 2013 along with English translation of claims and relevant portion of remarks made in Amendment.
Office Action from Japanese Application No. 2010-511374 dated Dec. 28, 2012.
Response from Japanese Application No. 2010-511374 dated Jul. 5, 2013 along with English translation of claims and relevant portion of remarks made in Amendment.
Office Action from European Application No. 05757183.8 dated Nov. 16, 2015.
Response to Office Action from European Application No. 05757183.8 dated Mar. 17, 2016.
Cook Medical brochure pages, Esophageal/Gastric Colonic: Snares, 3 pgs., date is at least as early as Jul. 1, 2013.
Juan-Marie et al. Double-Lumen Snare Injector: Introducing the Double-Lumen Concept in Ancillary Pollypectomy Equipment, Gastrointestinal Endoscopy, vol. 57, No. 5, 2003.
MTW Endoskopie, brochure, one page, date is at least as early as Jul. 1, 2013.
Olympus, EndoTherapy, Polypectomy, brochure, 3 pgs., date is at least as early as Jul. 1, 2013.
English translation of Office Action in Japanese Application No. 2014-004359 dated Jan. 20, 2015.
Extended European Search Report in European Application No. 08756773.1 dated Feb. 23, 2015.
Office Action from U.S. Appl. No. 14/565,024 dated Dec. 9, 2015.
Extended European Search Report in European Application No. 08714094.3 dated Jan. 27, 2016.
International Search Report and Written Opinion from PCT/US02/15465 dated Aug. 26, 2003.
International Preliminary Examination Report from PCT/US02/15465 dated Nov. 12, 2003.
International Search Report from and Written Opinion from PCT/US05/18294 dated Jul. 23, 2007, 6 pgs.
International Search Report and Written Opinion from PCT/US05/18497 dated May 8, 2008.
International Search Report and Written Opinion from PCT/US08/52342 dated Jul. 30, 2008.
International Search Report and Written Opinion from PCT/US08/066161 dated Sep. 22, 2008.
International Search Report and Written Opinion from PCT/US2014/053828 dated Dec. 30, 2014.
International Preliminary Report on Patentability from PCT/US2014/053828 dated Mar. 8, 2016.
Office Action from U.S. Appl. No. 11/137,814 dated May 16, 2007.
Response from U.S. Appl. No. 11/137,814 dated Aug. 16, 2007.
Office Action from U.S. Appl. No. 11/137,814 dated Dec. 7, 2007.
Response from U.S. Appl. No. 11/137,814 dated Apr. 7, 2008.
Office Action from U.S. Appl. No. 11/137,814 dated Jul. 18, 2008.
Response from U.S. Appl. No. 11/137,814 dated Sep. 18, 2008.
Interview Summary and Advisory Action from U.S. Appl. No. 11/137,814 dated Oct. 14, 2008.
Response from U.S. Appl. No. 11/137,814 dated Nov. 18, 2008.
Office Action from U.S. Appl. No. 11/137,814 dated Feb. 12, 2009.
Response from U.S. Appl. No. 11/137,814 dated Aug. 12, 2009.
Office Action from U.S. Appl. No. 11/137,814 dated Nov. 23, 2009.
Response from U.S. Appl. No. 11/137,814 dated Jan. 19, 2010.
Notice of Allowance from U.S. Appl. No. 11/137,814 dated Feb. 18, 2010.
Office Action from U.S. Appl. No. 11/404,345 dated Jun. 27, 2008.
Interview Summary from U.S. Appl. No. 11/404,345 dated Oct. 7, 2008.
Response from U.S. Appl. No. 11/404,345 dated Nov. 26, 2008.
Office Action from U.S. Appl. No. 11/404,345 dated Mar. 11, 2010.
Response from U.S. Appl. No. 11/404,345 dated May 11, 2010.
Advisory Action from U.S. Appl. No. 11/404,345 dated May 27, 2010.
Response from U.S. Appl. No. 11/404,345 dated Sep. 13, 2010.
Office Action from U.S. Appl. No. 11/404,345 dated Dec. 29, 2010.
Response from U.S. Appl. No. 11/404,345 dated May 25, 2011.
Notice of Allowance from U.S. Appl. No. 11/404,345 dated Aug. 19, 2011.
Office Action from U.S. Appl. No. 12/021,903 dated Dec. 10, 2009.
Response from U.S. Appl. No. 12/021,903 dated Jun. 9, 2010.
Office Action from U.S. Appl. No. 12/021,903 dated Aug. 5, 2010.
Response from U.S. Appl. No. 12/021,903 dated Oct. 7, 2010.
Interview Summary from U.S. Appl. No. 12/021,903 dated Oct. 5, 2010.
Office Action from U.S. Appl. No. 12/021,903 dated Dec. 29, 2011.
Interview Summary from U.S. Appl. No. 12/021,903 date Mar. 21, 2012.
Response from U.S. Appl. No. 12/021,903 dated May 25, 2012.
Notice of Allowance from U.S. Appl. No. 12/021,903 dated Aug. 9, 2012.
Notice of Allowance from U.S. Appl. No. 12/021,903 dated Nov. 20, 2012.
Office Action from U.S. Appl. No. 14/016,906 dated Apr. 8, 2015.
Response to Office Action from U.S. Appl. No. 14/016,906 dated Feb. 12, 2016.
Office Action from U.S. Appl. No. 14/016,906 dated May 31, 2016.
Response to Office Action from U.S. Appl. No. 14/016,906 dated Jul. 28, 2016.
Office Action from U.S. Appl. No. 14/016,906 dated Sep. 13, 2016.
Response to Office Action from U.S. Appl. No. 14/016,906 dated Dec. 13, 2016.
Office Action from U.S. Appl. No. 14/565,024 dated Apr. 17, 2015.
Response to Office Action from U.S. Appl. No. 14/565,024 dated Aug. 17, 2015.
Response to Office Action from U.S. Appl. No. 14/565,024 dated Mar. 25, 2016.
Office Action from U.S. Appl. No. 14/016,906 dated Mar. 10, 2017.
International Search Report and Written Opinion from PCT/US18/13017 dated Apr. 6, 2018.
Communication Pursuant to Artile 94(3) EPC from European Application No. 05755966.8 dated Oct. 22, 2018.
English Translation of Office Action from Japanese Patent Application No. 2016-0540331 dated May 29, 2018.
Extended Search Report from European Application No. 18167984.6 dated Jul. 30, 2018.
Communication Pursuant to Article 94(3) from European Application No. 18167984.6 dated Jun. 6, 2019.
Notice of Allowance from U.S. Appl. No. 15/866,401 dated Jan. 23, 2020.
Notice of Allowance from U.S. Appl. No. 15/866,401 dated Mar. 18, 2020.

\* cited by examiner

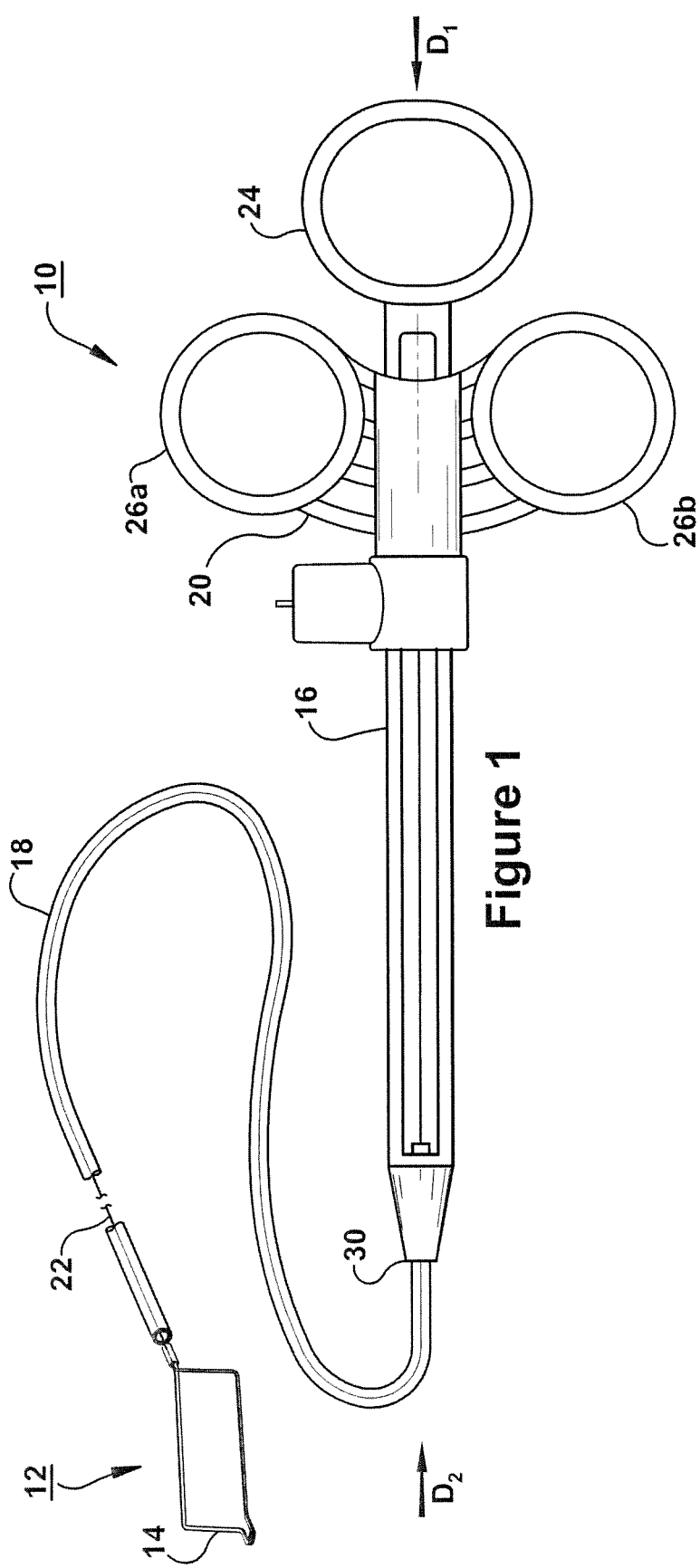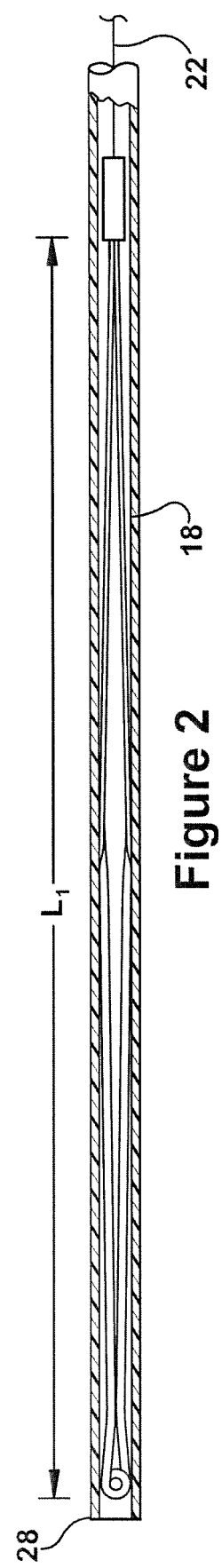
Figure 1
Figure 2

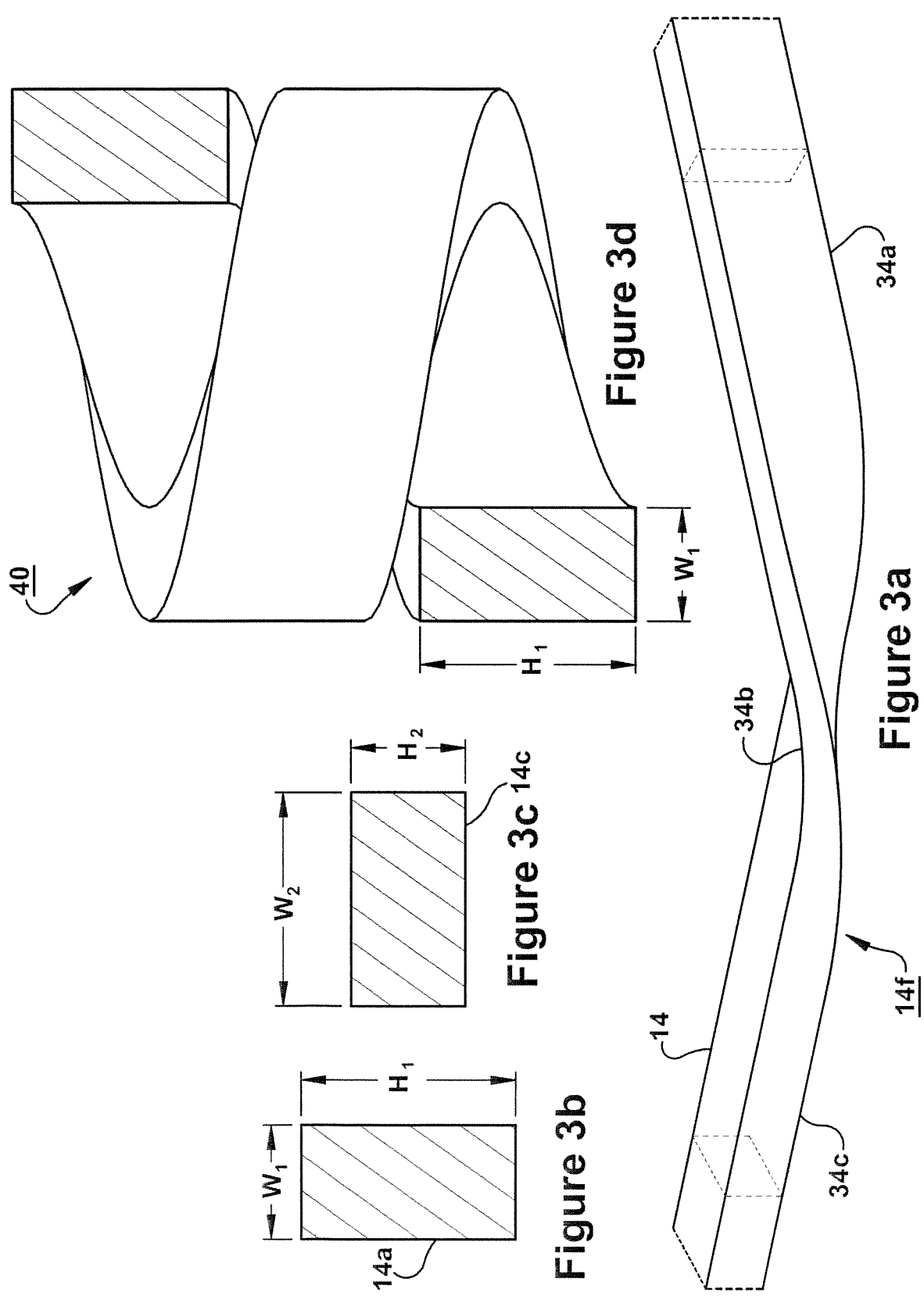

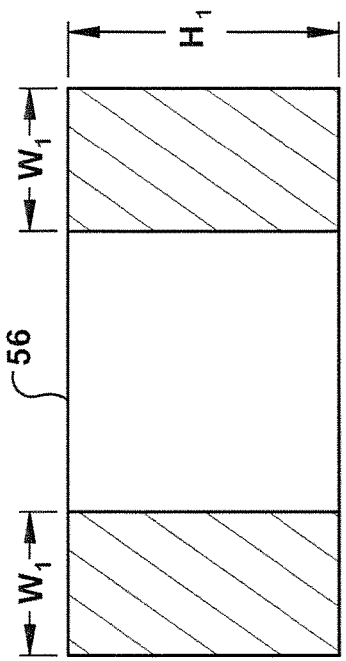
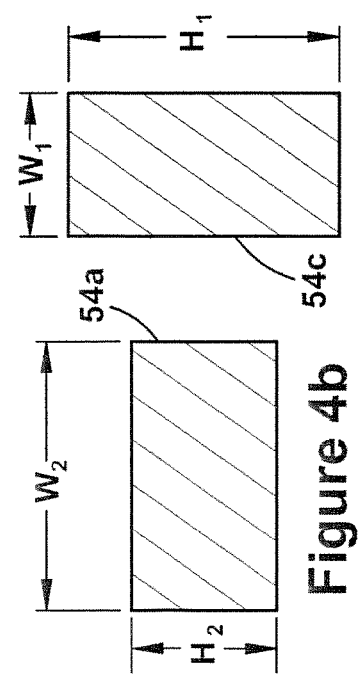
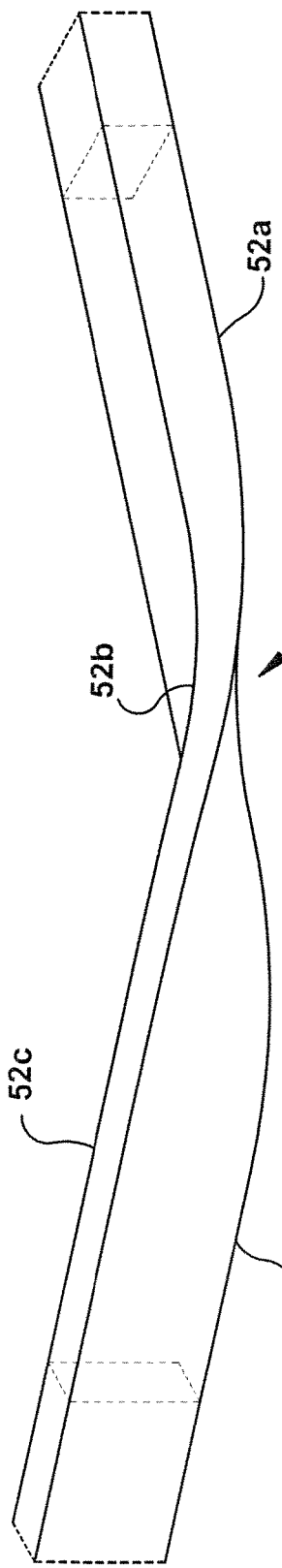
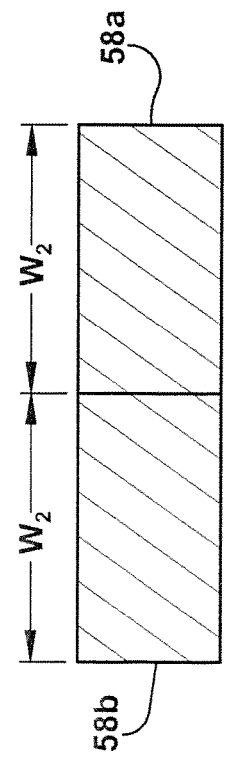
Figure 4a, Figure 4b, Figure 4c, Figure 4d, Figure 4e

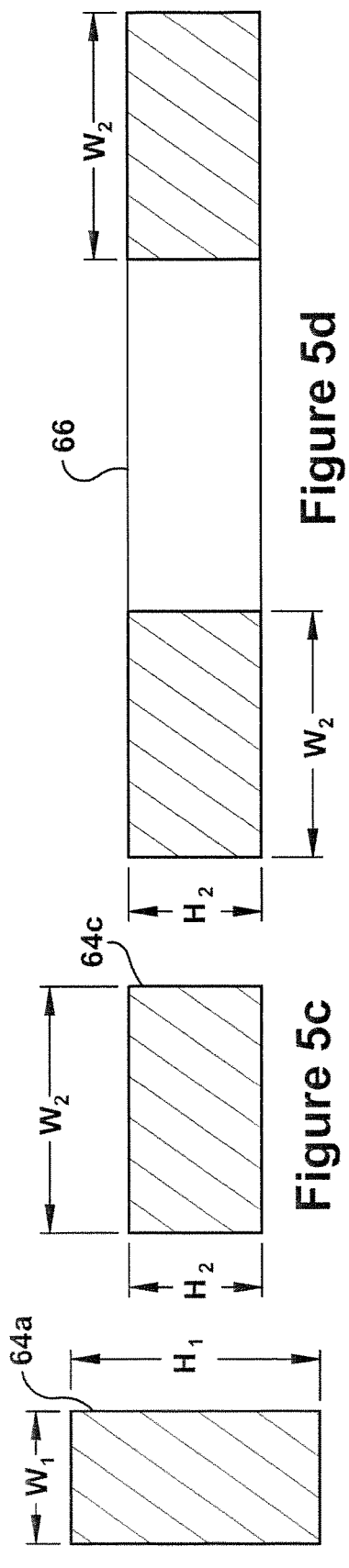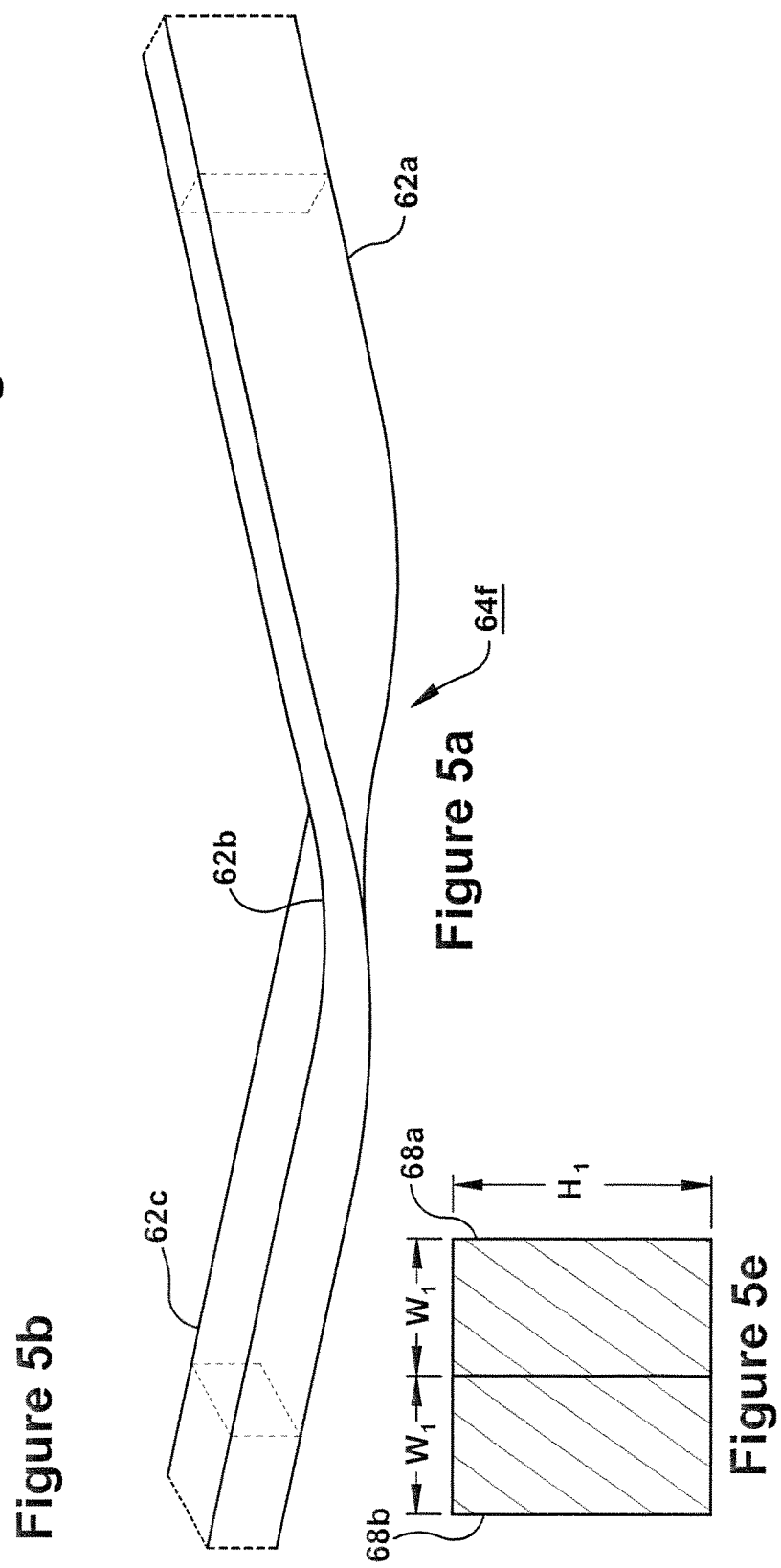

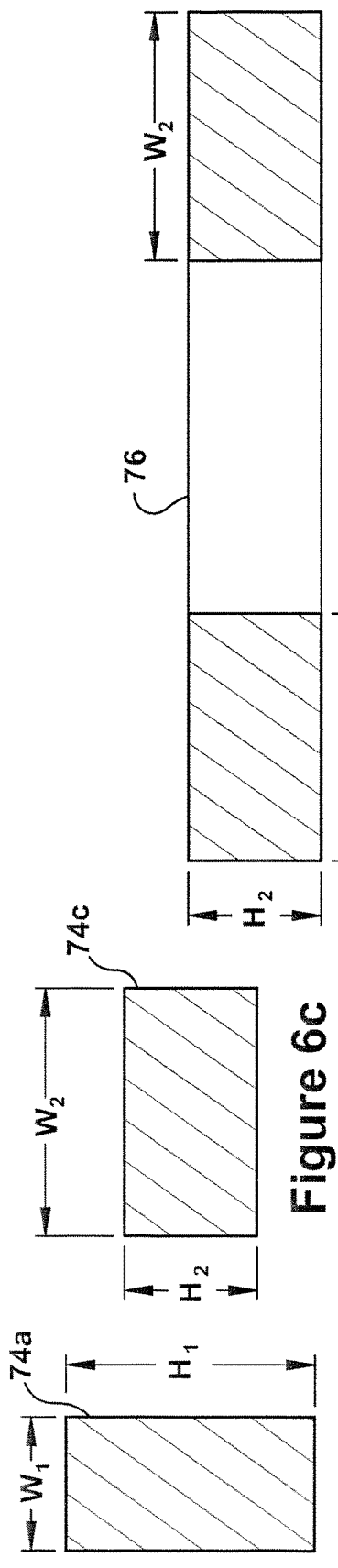
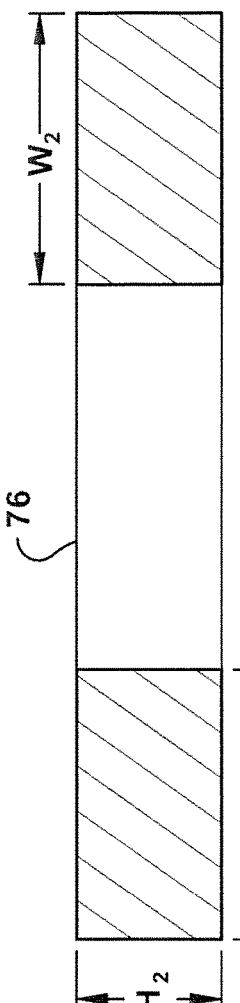
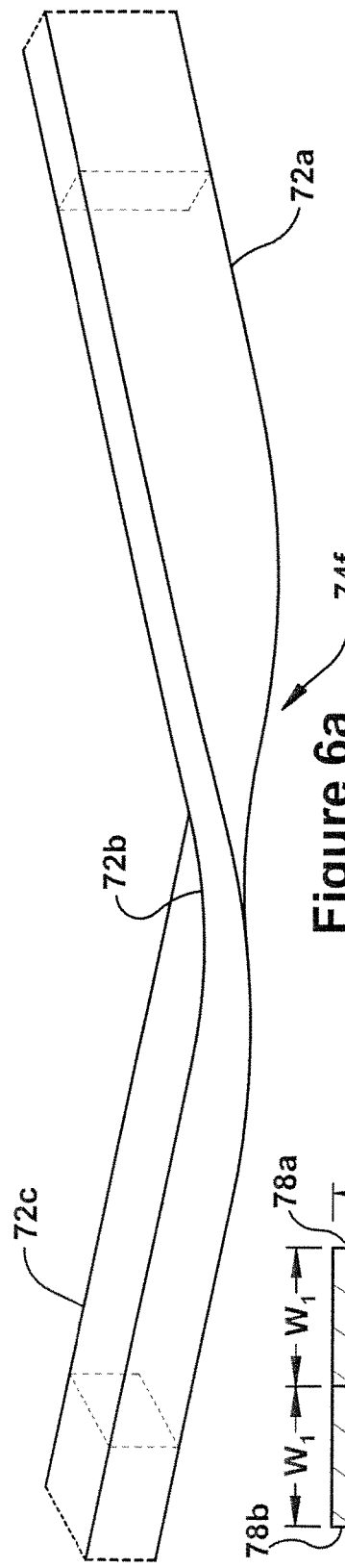
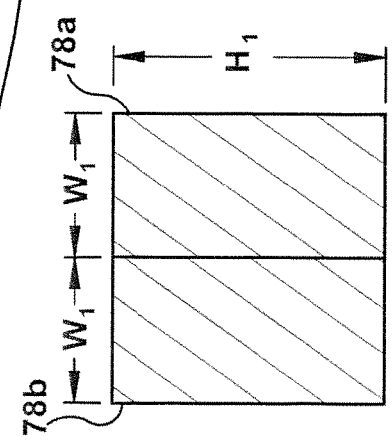

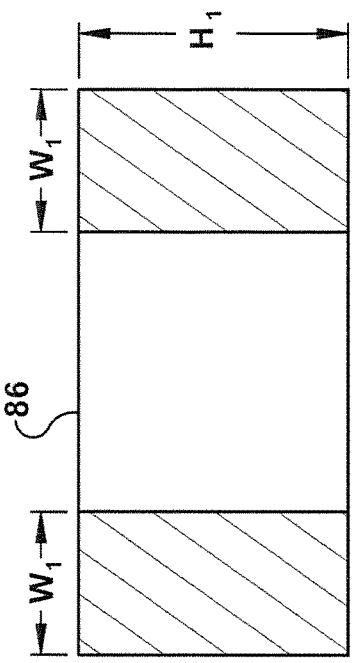
Figure 7d
Figure 7c
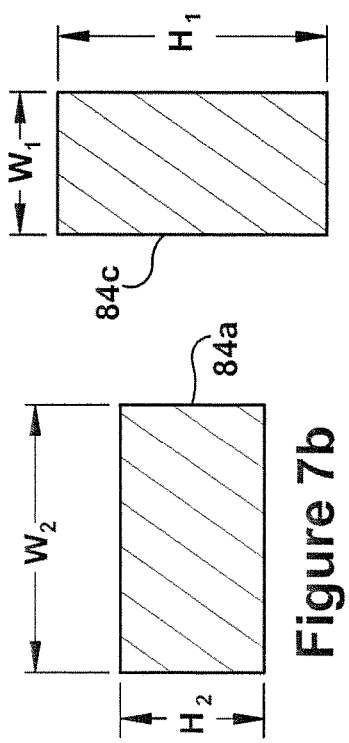
Figure 7b
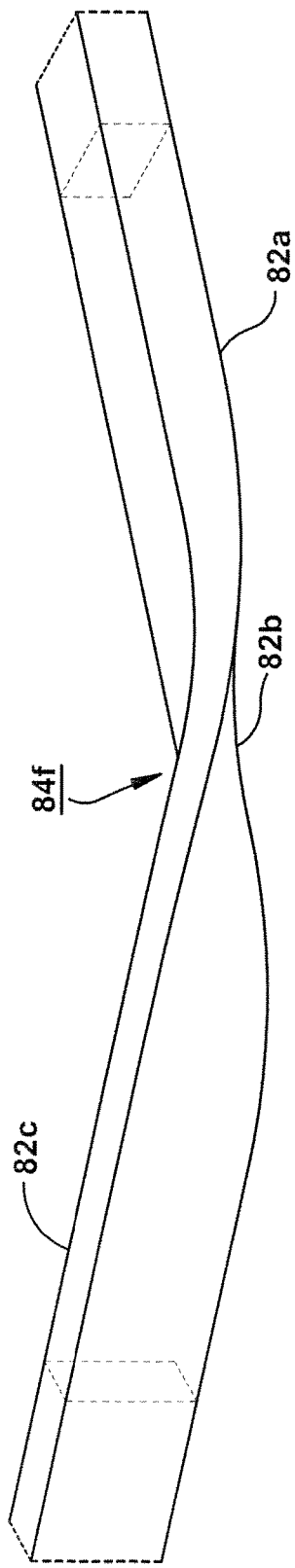
Figure 7a
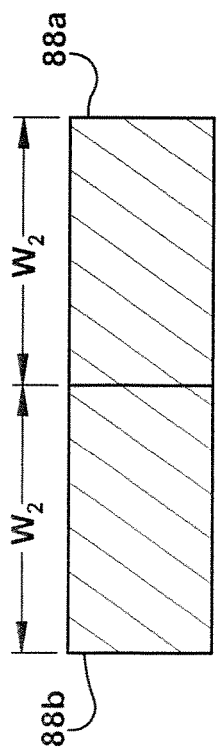
Figure 7e

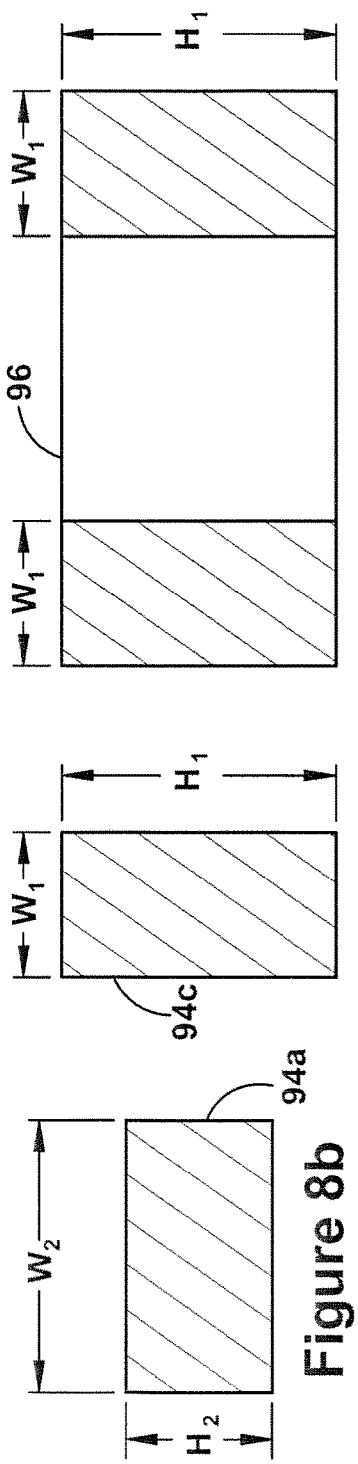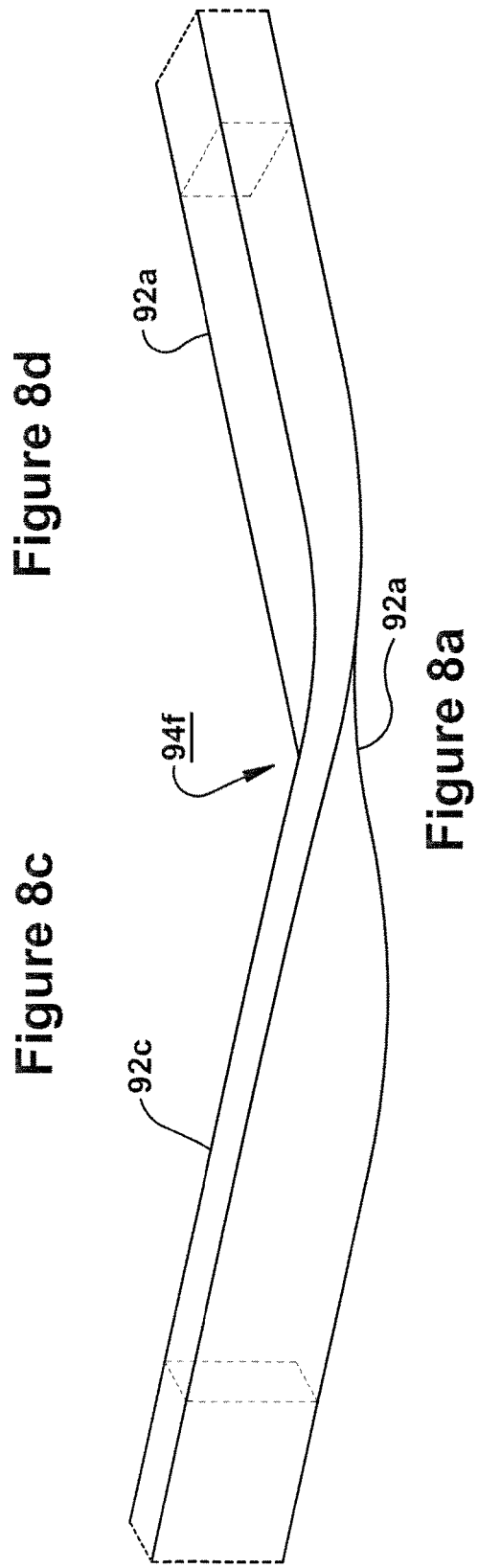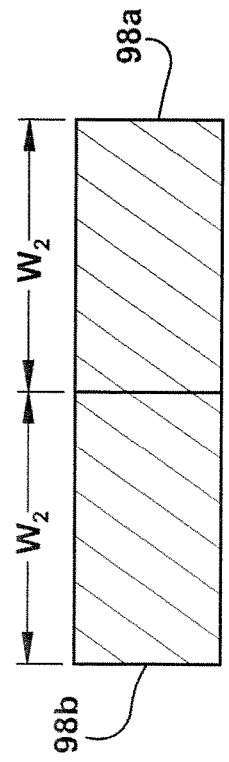
Figure 8d
Figure 8c
Figure 8b
Figure 8a
Figure 8e

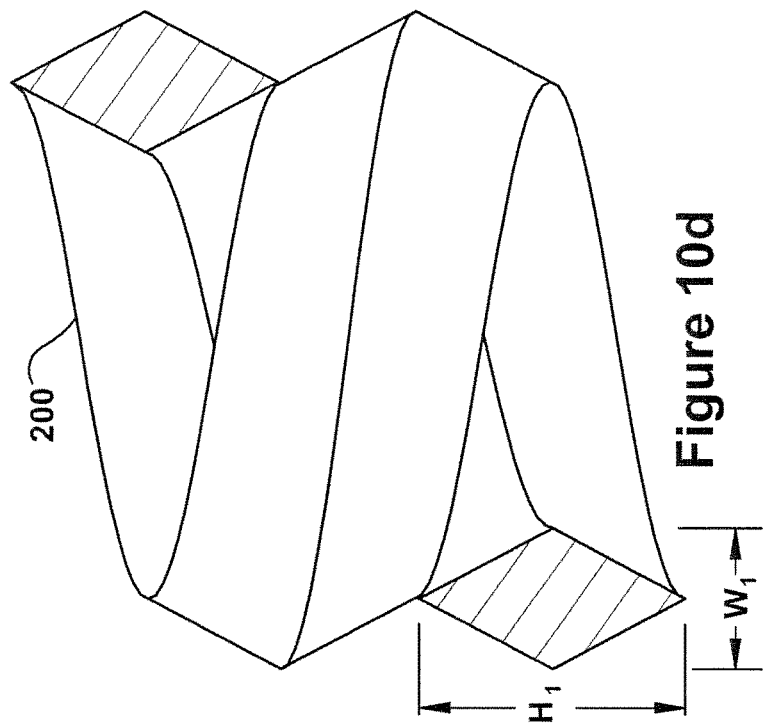
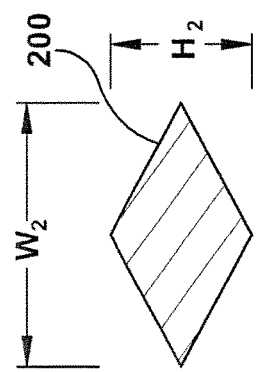
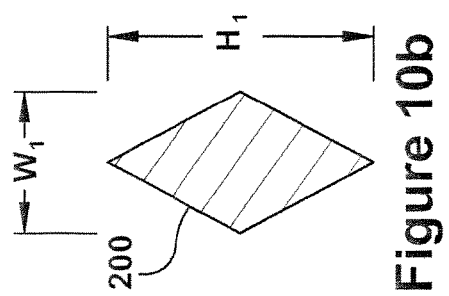
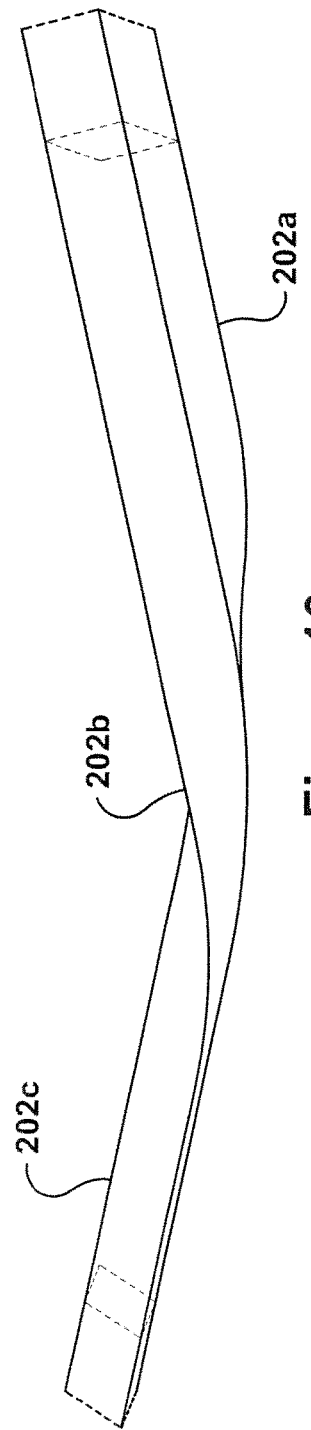

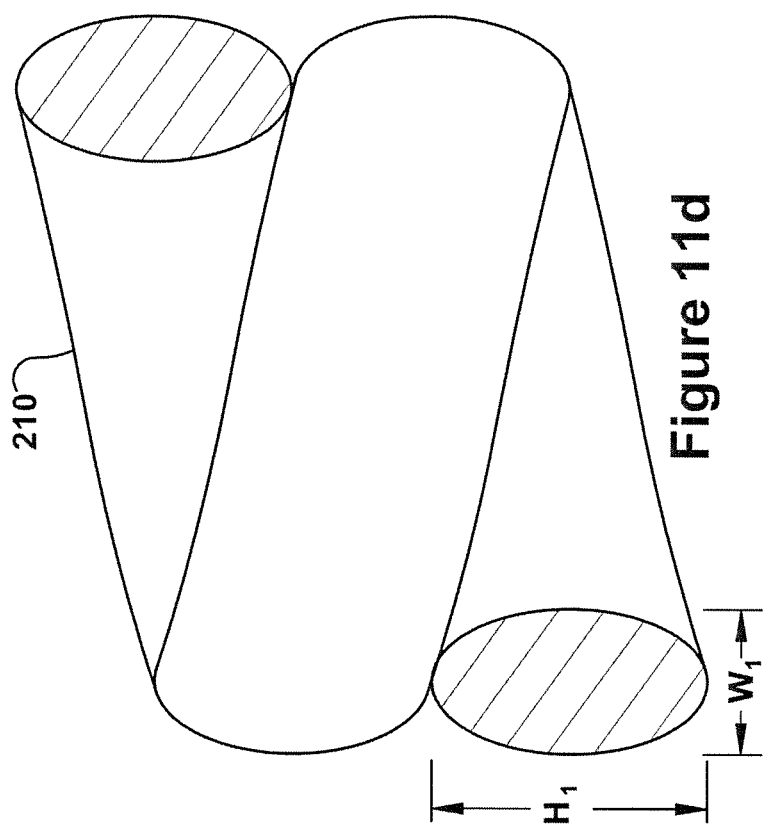
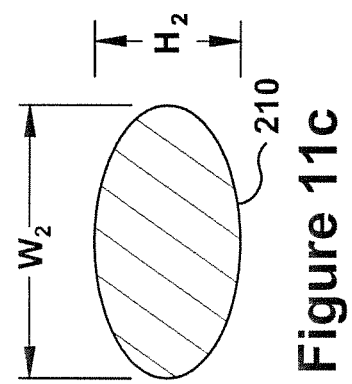
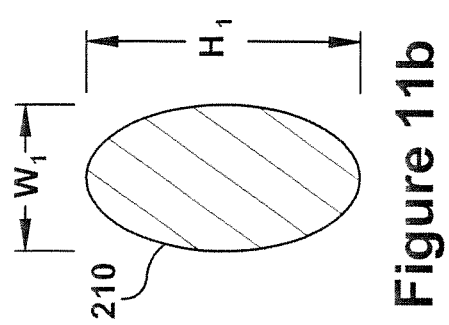
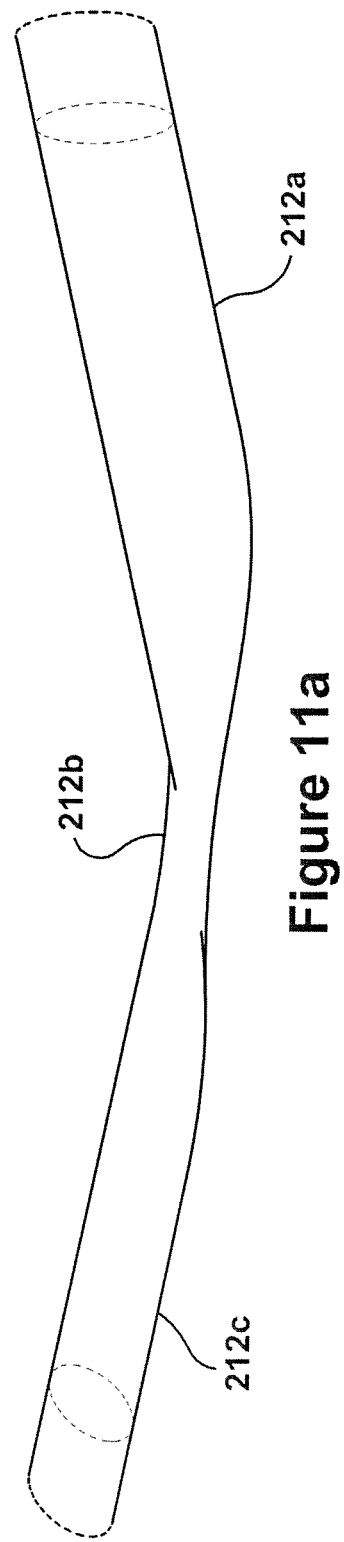
Figure 11a
Figure 11b
Figure 11c
Figure 11d

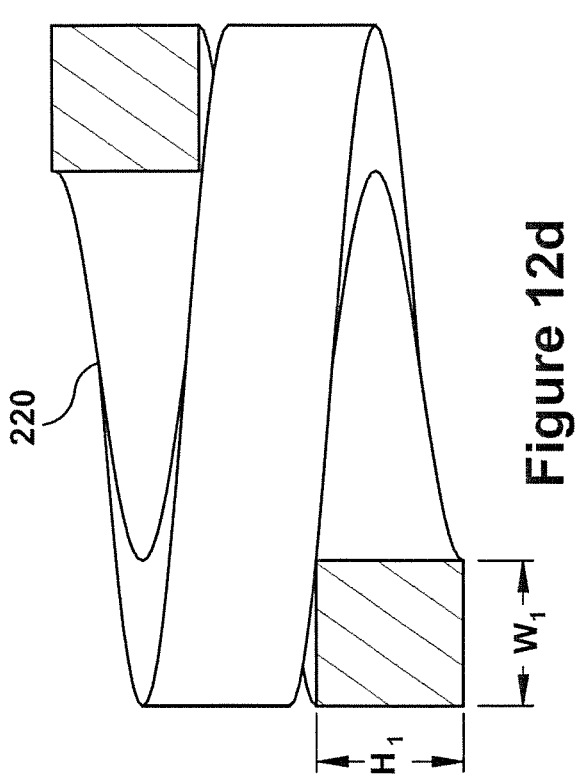
Figure 12d
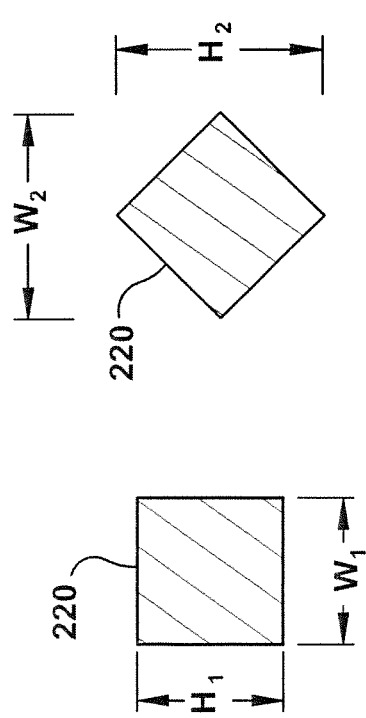
Figure 12c
Figure 12b
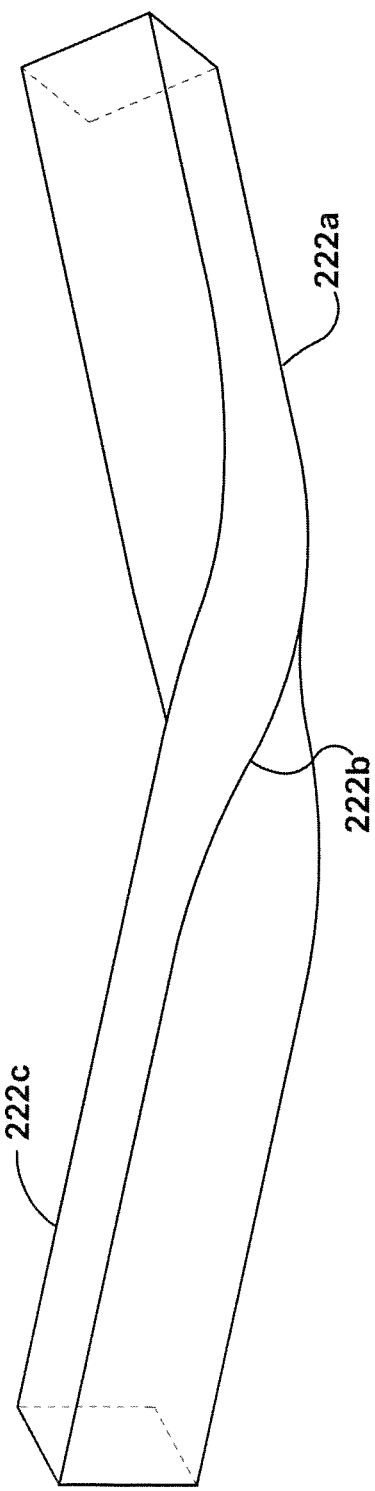
Figure 12a

ENDOSCOPIC SNARE DEVICE

CROSS-REFERENCE TO RELATED APPLICATION

This application is a continuation of U.S. application Ser. No. 14/565,024, filed Dec. 9, 2015, which is a continuation-in-part of U.S. application Ser. No. 14/016,906, titled "ENDOSCOPIC SNARE DEVICE," and filed on Sep. 3, 2013. The entire disclosures of the above referenced application are fully incorporated herein by reference.

BACKGROUND

Endoscopes are well-known in the medical arts and are commonly used for numerous medical procedures. One such procedure is removing targeted tissue from the gastrointestinal mucosal wall of a human subject. Various types of tissue, such as for example, polyps, lesions, tumors or adenomas, may be removed for various medical purposes, such as for example, treatment or diagnostic testing.

One conventional polypectomy technique for removing targeted tissue is cauterization. For example, cauterizing devices may be used to remove an unwanted polyp. A cauterizing device uses heat to separate the targeted tissue from the gastrointestinal wall of a patient. The removed tissue may be discarded or captured for testing.

Mechanical devices, such as for example, snares, are also known in the art. For example, a snare may be used to separate a polyp from the gastrointestinal wall of a patient. Specifically, an operator may deploy or open a snare loop, and position the snare around a polyp. By retrieval or closing of the snare loop, the operator can cut into the tissue and separate the tissue from the gastrointestinal wall. Subsequently, the operator may use a suction source to capture and retain the tissue after separation from the wall.

SUMMARY

The present application describes a tissue removal tool for use with an endoscope, such as for example, a snare suitable for use in removing a gastrointestinal polyp.

In an exemplary embodiment, the tool includes a loop. The loop is movable between an open position and a closed position. The loop is advantageously shaped in the open position for tissue removal and includes-collapse resistant bends.

Further features and advantages of the invention will become apparent from the following detailed description made with reference to the accompanying drawings.

BRIEF DESCRIPTION OF THE DRAWINGS

Features and advantages of the general inventive concepts will become apparent from the following detailed description made with reference to the accompanying drawings.

FIG. 1 is a perspective view of a retrieval device, showing a snare in an open position;

FIG. 2 is an enlarged sectional view of a portion of the retrieval device of FIG. 1, showing the snare in a closed position within a conduit;

FIG. 3a is an enlarged perspective view of the designated circular area of FIG. 3;

FIG. 3b is sectional view of the snare of FIG. 3, shown along the line 3b-3b of FIG. 3;

FIG. 3c is sectional view of the snare of FIG. 3, shown along the line 3c-3c of FIG. 3;

FIG. 3d is sectional view of the snare of FIG. 3, shown along the line 3d-3d of FIG. 3;

FIG. 4a is an enlarged perspective view of the designated circular area of FIG. 4;

FIG. 4b is sectional view of the snare of FIG. 4, shown along the line 4b-4b of FIG. 4;

FIG. 4c is sectional view of the snare of FIG. 4, shown along the line 4c-4c of FIG. 4;

FIG. 4d is sectional view of the snare of FIG. 4, shown along the line 4d-4d of FIG. 4;

FIG. 4e is sectional view of the snare of FIG. 4, shown along the line 4e-4e of FIG. 4;

FIG. 5a is an enlarged perspective view of the designated circular area of FIG. 5;

FIG. 5b is sectional view of the snare of FIG. 5, shown along the line 5b-5b of FIG. 5;

FIG. 5c is sectional view of the snare of FIG. 5, shown along the line 5c-5c of FIG. 5;

FIG. 5d is sectional view of the snare of FIG. 5, shown along the line 5d-5d of FIG. 5;

FIG. 5e is sectional view of the snare of FIG. 5, shown along the line 5e-5e of FIG. 5;

FIG. 6a is an enlarged perspective view of the designated circular area of FIG. 6;

FIG. 6b is sectional view of the snare of FIG. 6, shown along the line 6b-6b of FIG. 6;

FIG. 6c is sectional view of the snare of FIG. 6, shown along the line 6c-6c of FIG. 6;

FIG. 6d is sectional view of the snare of FIG. 6, shown along the line 6d-6d of FIG. 6;

FIG. 6e is sectional view of the snare of FIG. 6, shown along the line 6e-6e of FIG. 6;

FIG. 7a is an enlarged perspective view of the designated circular area of FIG. 7;

FIG. 7b is sectional view of the snare of FIG. 7, shown along the line 7b-7b of FIG. 7;

FIG. 7c is sectional view of the snare of FIG. 7, shown along the line 7c-7c of FIG. 7;

FIG. 7d is sectional view of the snare of FIG. 7, shown along the line 7d-7d of FIG. 7;

FIG. 7e is sectional view of the snare of FIG. 7, shown along the line 7e-7e of FIG. 7;

FIG. 8a is an enlarged perspective view of the designated circular area of FIG. 8;

FIG. 8b is sectional view of the snare of FIG. 8, shown along the line 8b-8b of FIG. 8;

FIG. 8c is sectional view of the snare of FIG. 8, shown along the line 8c-8c of FIG. 8;

FIG. 8d is sectional view of the snare of FIG. 8, shown along the line 8d-8d of FIG. 8;

FIG. 8e is sectional view of the snare of FIG. 8, shown along the line 8e-8e of FIG. 8;

FIG. 10a is perspective view of a portion of a snare having a diamond-shape, shown in a similar orientation as the snare in FIG. 3a;

FIG. 10b is a sectional view of the snare of FIG. 10a, shown in an orientation similar to the sectional view of FIG. 3b;

FIG. 10c is a sectional view of the snare of FIG. 10a, shown in an orientation similar to the sectional view of FIG. 3c;

FIG. 10d is a sectional view of the snare of FIG. 10a, shown in an orientation similar to the sectional view of FIG. 3d;

FIG. 11a is perspective view of a portion of a snare having an oval-shape, shown in a similar orientation as the snare in FIG. 3a;

FIG. 11b is a sectional view of the snare of FIG. 11a, shown in an orientation similar to the sectional view of FIG. 3b;

FIG. 11c is a sectional view of the snare of FIG. 11a, shown in an orientation similar to the sectional view of FIG. 3c;

FIG. 11d is a sectional view of the snare of FIG. 11a, shown in an orientation similar to the sectional view of FIG. 3d;

FIG. 12a is perspective view of a portion of a snare having a square-shape, shown in a similar orientation as the snare in FIG. 3a;

FIG. 12b is a sectional view of the snare of FIG. 12a, shown in an orientation similar to the sectional view of FIG. 3b;

FIG. 12c is a sectional view of the snare of FIG. 12a, shown in an orientation similar to the sectional view of FIG. 3c;

FIG. 12d is a sectional view of the snare of FIG. 12a, shown in an orientation similar to the sectional view of FIG. 3d;

DETAILED DESCRIPTION

Figure 3:
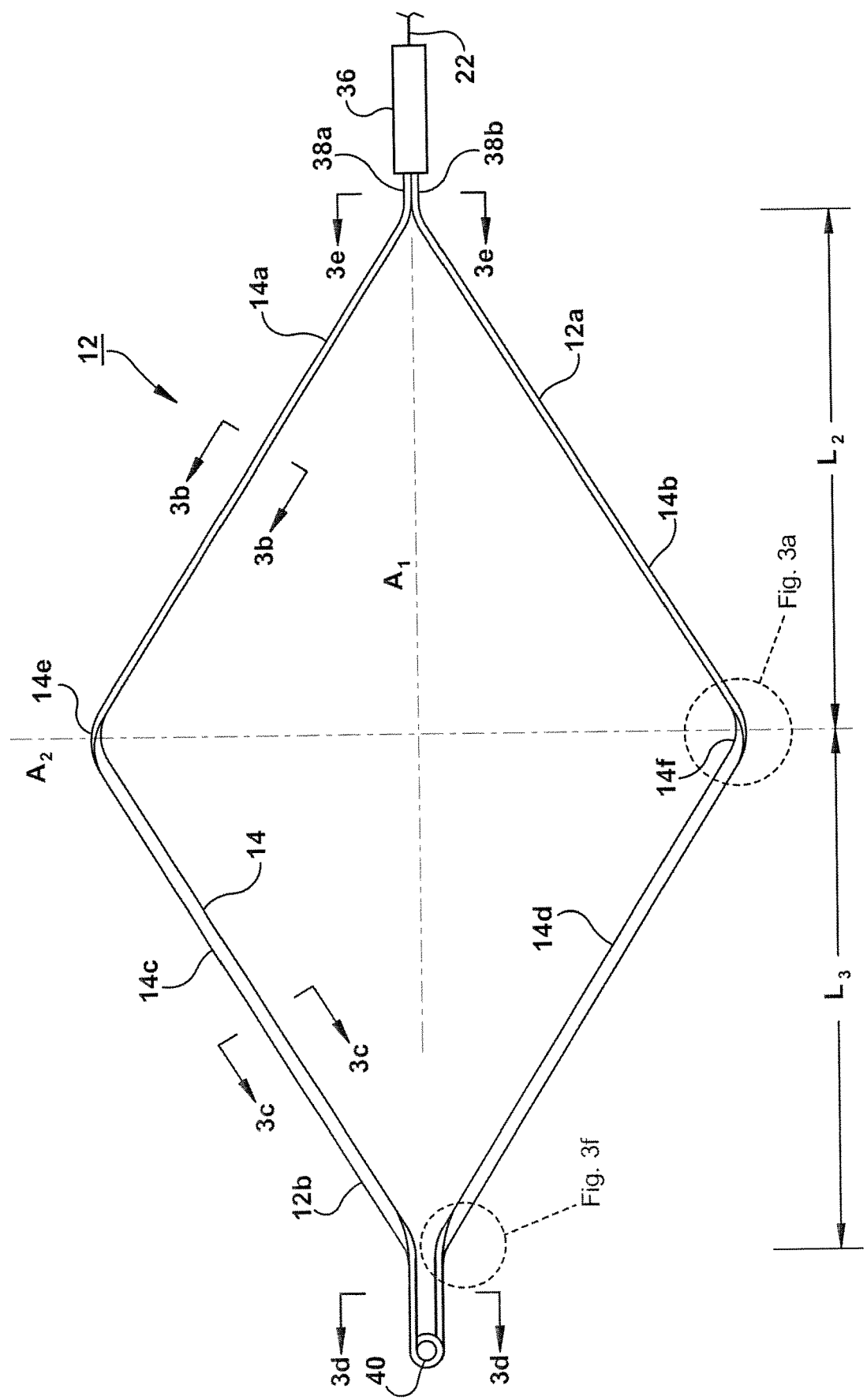
FIG. 3 is a top view of the snare of FIG. 1, showing the snare in an open or deployed position.
Figure 3E:
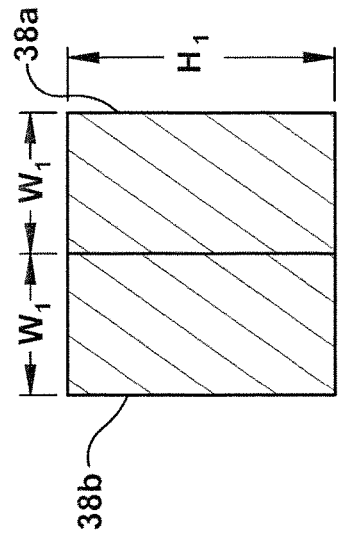
FIG. 3e is sectional view of the snare of FIG. 3, shown along the line 3e-3e of FIG. 3.

This Detailed Description merely describes exemplary embodiments in accordance with the general inventive concepts and is not intended to limit the scope of the invention or the claims in any way. Indeed, the invention as described by the claims is broader than and unlimited by the exemplary embodiments set forth herein, and the terms used in the claims have their full ordinary meaning.

The general inventive concepts will now be described with occasional reference to the exemplary embodiments of the invention. This general inventive concept may, however, be embodied in different forms and should not be construed as limited to the embodiments set forth herein. Rather, these embodiments are provided so that this disclosure will be thorough and complete, and will fully convey the scope of the general inventive concepts to those skilled in the art.

Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts. As used in this detailed description and the appended claims, the singular forms "a," "an," and "the" are intended to include the plural forms as well, unless the context clearly indicates otherwise.

Unless otherwise indicated, all numbers, such as for example, numbers expressing measurements or physical characteristics, used in the specification and claims are to be understood as being modified in all instances by the term "about." Accordingly, unless otherwise indicated, the numerical properties set forth in the specification and claims are approximations that may vary depending on the suitable properties sought to be obtained in embodiments of the invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

When generally discussing the invention and embodiments of the invention, the terms "portrait" and "landscape" will be used to described an orientation of an object. The term "portrait" and the term "landscape" have their common ordinary meaning, and are used in the same manner in which one would use each term to describe the orientation of a common and well-known object or thing, such as for example, a piece of paper or a picture frame.

Several limitations exist with conventional polypectomy removal techniques. Despite careful use, cauterization devices may cause serious thermal injury to the gastrointestinal wall, fail to remove the entire targeted tissue, or do not completely cauterize blood vessels which lead to excessive bleeding. Mechanical snare devices may also be difficult to operate, and a physician may experience difficulty in securing the targeted tissue with the snare. Also, snaring only the minimal tissue required from the three-layer wall, i.e., mucosa, submucosa, and muscularis, is also important. More specifically, to prevent complications, the muscularis tissue should be avoided in a mechanical snaring procedure.

An operator's attempt to minimize unwanted damaged to the removal site is complicated by a conventional snare. An operator of a snare may have difficulty in maintaining the snare in a flat position, that is to say, level or parallel with respect to the gastrointestinal wall, when closing the snare, and the desired tissue becomes more difficult to capture. A conventional snare tends to rise up and off the targeted tissue, or skim along the top of the tissue, when the snare is closing and moving in a proximal direction. As a result, either none or an inadequate amount of the targeted tissue is captured. Consequently, the snare has to be reopened and placed again on the distal side of the targeted tissue, and the process repeated until an adequate amount of tissue is captured. Furthermore, each opening and closing of the snare may lead to deformities in the snare. Such deformities may cause difficulties in fully opening the snare or may cause the snare to unexpectedly collapse during tissue capture.

Some physicians have used other techniques to improve results of a snare capture, especially on a first attempt. For example, some technicians use an endoscopic needle tool to inject saline into the targeted tissue. The injected saline increases the size of the targeted tissue, and in some cases, makes the tissue an easier target for a conventional snare process. This injection step adds time and cost, both labor and material, to the overall procedure.

The present application describes a tissue removal tool for use with an endoscope, such as for example, a snare suitable for use in removing a tissue sample, such as for example, a gastrointestinal polyp. The tool offers improved performance features, such as for example, moving the polyp into a raised and pinched position such that the polyp may be transected with a snare which remains in essentially a flat position.

The polyp may be advantageously manipulated in either the deployment direction, the retrieval direction, or both. The snare is formed by a wire, or similar structure, and arranged and shaped such to have a proximal portion and a distal portion in a deployed position. The proximal portion and a distal portion have different shapes in relation to each other, and specifically, in relation to the cross-sectional shape of one portion in relation to the cross-sectional shape of the other portion. The contrasting shape of one portion of the loop in relation to the other has surprising and previously unknown benefits. The proximal portion and the distal portion may be separated by a transition portion, in which the wire changes orientation, such as for example, is twisted, such that the cross-sectional shape of the wire is different in the proximal portion as compared to the distal portion. In other words, the piece of wire may have a cross-sectional height in the proximal portion unequal to a cross-sectional height in the distal portion. The wire may have a cross-sectional height in the proximal section equal to a cross-sectional width in the distal portion. Thus, in one of the deployment direction or the retrieval direction, the polyp is raised or pinched, and in the other of the deployment direction or the retrieval direction, the polyp is cut along a straight line relative the gastro-intestinal wall.

The snare may be shaped to perform the same or similar in other embodiments of the invention. The snare loop may be formed by a proximal portion, a distal portion, and a transitional portion separating the proximal portion and the distal portion. The piece of wire may be twisted by at least 45 degrees in the transitional portion on at least one side of the loop. As such, the piece of wire may have a cross-sectional height larger than a cross-sectional width in the proximal portion and a cross-sectional width larger than a cross-sectional height in the distal portion. Alternatively, the piece of wire may have a cross-sectional height smaller than a cross-sectional width in the proximal portion and a cross-sectional width smaller than a cross-sectional height in the distal portion.

In another embodiment of the invention, the shape of the loop may include portions which act as a memory point during opening and closing of the loop by motion of the handle relative the body. For example, the shape of the loop may be at least partially defined by a rotated and bent wire portion on either side of the loop, wherein the piece of wire has a cross-sectional height larger than a cross-sectional width at a location proximal to either rotated and bent wire portion and a cross-sectional height smaller than a cross-sectional width at a location distal to either rotated and bent wire portion. In one embodiment, the loop is polygon-shaped in the open position and the piece of wire is twisted essentially 90 degrees in the rotated and bent portion.

As discussed herein, the invention offers performance features related to preparing the polyp for removal. In one embodiment, the shape of the loop is defined by a distal portion and a proximal portion. The proximal portion has a distal facing vertical face and the distal position has a proximal facing edge. The wire forming the loop is twisted between the proximal portion and the distal portion, such that the distal facing vertical face of the proximal portion is higher than the proximal facing edge of the distal portion, and the top horizontal face of the distal portion is wider than a top horizontal face of the proximal portion. In deployment, the distal facing vertical face of the proximal portion pushes against the polyp. In retrieval, the proximal facing vertical edge of the distal portion cuts into the polyp as distal facing vertical face of the proximal portion prohibits movement of the polyp in the proximal direction. In other words, the proximal portion raises and pinches the polyp to prepare the polyp for transecting. Specifically, the proximal portion may increase the percentage of the polyp which is above a targeted cutting line, relative the gastro-intestinal wall.

A method of using an endoscopic tool to collect a tissue sample is also disclosed. The method includes placing a loop of an endoscopic tool adjacent a targeted tissue sample. The loop is formed by a piece of wire and is movable between a closed position and a deployed position by use of a tool handle. The distal facing vertical inward face of the proximal portion is higher than proximal facing inward edge of the distal portion.

In the performance of the method, the operator moves the loop from a closed position to an open position. In the open or deployed position, the distal facing vertical inward face of the proximal portion pushes against the targeted tissue sample. After full or otherwise desired deployment, the loop is moved from the open or deployed position to a closed position, such that the proximal facing vertical inward edge of the distal portion cuts into the targeted tissue sample. The method allows a snare to transect a polyp in the retrieval direction without the snare riding up the distal side of the polyp. A snare riding up the polyp may prohibit cutting the polyp along a straight line, or parallel line, relative the gastro-intestinal wall.

Referring now to the drawings, a retrieval device, or tissue removal tool is illustrated in FIG. 1. The tool is arranged for use with an endoscope to remove a tissue sample from the gastrointestinal wall of a human patient. The tool is also usable for other scientific purposes, and with a combination of other devices. This tool is illustrated and discussed for exemplary purposes only, and the invention may be practice with a tool having characteristics which vary from this tool.

The exemplary tool 10 includes a loop 12 formed by a piece of wire 14. A wire of any suitable material may be used to form the loop, such as for example, a metal, such as stainless steel, or a plastic. The variations in the wire shape and orientation along the length of the wire may be made by mechanically twisting a preformed wire into the desired shape and orientation, of the wire may be originally manufactured to have the desired shape and orientation, such as for example, a preformed plastic piece. A suitable material will be flexible and have memory to allow deployment and retrieval of the loop. The wire forms a plurality of segments separated by collapse-resistant bends to define a loop opening. The loop is movable between an open position, or deployed position, and a closed position, or retrieved position. The loop 12 is illustrated in an open position in FIG. 1. The loop is polygon-shaped, and specifically, the loop is generally diamond-shaped. In FIG. 2, the loop 12 is shown in a closed position within a distal portion of the tool 10. As discussed herein, the loop 12 is within a conduit 18. In this closed or retrieved position, the exemplary loop has a length $L_1$.

The tool may include a support assembly and a transmitting system for moving the loop between an open position and a closed position. In the exemplary tool 10 illustrated in FIG. 1, the support assembly includes a base or body 16 and an elongated hollow tube, tubular member or conduit 18. The transmitting assembly includes a handle 20 movable relative to the body 16 and a link 22. One end of the link is fixed to the handle and a second end is remote from the body. As shown in FIGS. 1 and 2, the link 22 extends substantially through a length of the conduit 18. The conduit 18 may be any suitable, small-diameter tube formed of a non-reactive low-friction flexible material, such as for example, polytetraflouroethylene. The conduit 18 defines a lumen with an opening at a distal second end 28, as best seen in FIG. 2 which shows a cross-sectional view of a distal portion of the tool 10. A proximal first end 30 of the conduit is fixed to the body 16.

The handle allows an operator to move the loop back and forth between a deployed position, as shown in FIG. 1, and a closed position, as shown in FIG. 2. Referring again to FIG. 1, the body 16 includes a fixed ring 24 at a proximal end. The handle 20 may be slid by an operator relative the body 16 by use of the handle 20, and specifically, by use of one or both of two rings 26a, 26b. The handle 20 is mounted over an elongated section of the body 16 and is movable relative to the body in the direction $D_1$ to deploy the loop 12, or in an opposing direction $D_2$ to close the loop 12. For example, an operator may place a finger in each of the rings 26a, 26b and a thumb of the same hand in the body ring 24. By moving the two fingers in the direction $D_1$, an operator can move the handle 20 relative to the body 16. This movement of the handle will deploy the loop. In contrast, the handle 20 can be slid in the opposite direction $D_2$ by pulling one's fingers towards one's thumb to close the loop.

A link 22 is connected to the handle 20 for transferring axial motion from the handle 20 to other parts of the device. The link may be constructed of any suitable rigid material, and may be solid, hollow, or any suitable elongated object or combination of objects. The link may be one piece or formed from a series of pieces and connections, such as for example, hypodermic tubes, swage connections, and cables. The link 22 has a first end fixed to the handle 20 and a second end remote from the body 16. As shown in the drawings, the link extends substantially through the conduit 18.

Referring now to FIG. 3, a top view of the exemplary tool 10 of FIG. 1 is shown in an open or deployed position. In the deployed position, the shape of the loop 14 may be discussed in relation to a longitudinal axis $_{A1}$ and a lateral axis $_{A2}$. The longitudinal axis $_{A1}$ is defined along the longitudinal axis of the link 22 and the axis defines a first side of the loop 14a, 14c and a second side 14b, 14d. The loop 12 is essentially symmetric relative the longitudinal axis $_{A1}$. It should be apparent to those with skill in the art that the invention can be practiced with loops having a shape which are asymmetric relative the longitudinal axis $_{A1}$, such as for example, the exemplary loops shown in FIGS. 9a and 9c.

The loop 12 has a proximal portion 12a and a distal portion 12b when in the deployed position. As shown in FIG. 3, the lateral axis $A_2$ defines, or separates, the loop into a proximal portion having two wire portions 14a, 14b and a distal portion having two wire portions 14c, 14d. In this arrangement and relative to the lateral axis $A_2$, the shape of proximal portion 12a is symmetric to the shape of the distal portion 12b. It should be apparent to those with skill in the art that the invention can be practiced with loops having a shape which are asymmetric to the lateral axis $A_2$, such as for example, the exemplary loops shown in FIGS. 5-8, 9a-9c and 9f.

The proximal portion and distal portion can also be defined relative a transitional portion. As shown in FIG. 3, a transitional portion 14e, 14f on either side of the loop 12 is disposed between the proximal portion 12a and the distal portion 12b. An enlarged perspective view of the transitional portion 14f is illustrated in FIG. 3a. Within the transitional area 14f, the wire twists and turns. For discussion purposes, the wire 14 is discussed herein as traveling for the proximal portion 12a to the distal portion 12b. Within the transitional portion 14f, an entering portion 34a of the wire has a height greater than a width, in other words, the rectangular shape of the wire is in a portrait orientation. The bottom of the wire twists at a middle portion 34b inward along an axis of the wire, and the wire itself bends inward toward the longitudinal axis of the loop 12. In the inventive tool, the wire is twisted at least 45° in a transitional portion on at least one side of the loop. In exemplary transitional portion 14f shown, the wire is twisted about 90°. As such, an exiting portion 34c of the wire 14a has width greater than a height, in other words, the rectangular shape of the wire is in a landscape orientation.

As discussed herein, the proximal portion and the distal portion are each formed from a wire 14. The wire is orientated in the proximal portion in a different orientation than in the distal portion. In the exemplary loop 12 shown in FIG. 3, the wire 14 has a rectangular-shaped cross section. The cross-sectional shape of the wire 14, relative to a horizontal plane during application, varies at different locations of the loop, as shown at different locations of the loop in FIGS. 3a-3f. As discussed herein, the cross-sectional shape of the loop in the proximal portion relative to the cross-sectional shape of the loop in the distal portion contributes to the advantageous features on the tool 10.

FIG. 3b is sectional view of the wire in the proximal portion 12a of the loop 12, and shown along the line 3b-3b of FIG. 3. The wire has a height $H_1$ which is greater than the width $W_1$. With the wire in an opposite orientation, FIG. 3c is sectional view of the wire in the distal portion of the loop 12. The wire is shown along the line 3c-3c of FIG. 3. The wire has a height $H_2$ which is less than the width $W_2$. As such, the piece of wire having a cross-sectional height $H_1$ in the proximal portion equal to a cross-sectional width $W_2$ in the distal portion and unequal to a cross-sectional height in the distal portion $H_2$. It would be apparent to one with skill in the art that the orientation of the wire in the proximal portion relative the distal portion could be reversed, in other words, the portrait orientation could be in the distal portion and the landscape orientation could be in the proximal portion in the practice of the invention, such as for example, as illustrated in the loops in FIGS. 4, 7 and 8.

Other sections of the loop will now be discussed. The loop 12 is formed by a wire 14 connected to the link 22. The two ends on the wire 14 are fixed to the link 22 by any suitable technique, such as for example, by welding. As shown in FIG. 3 and in the cross-sectional view in FIG. 3e, the two end portions 38a, 38b are contiguous and each in a portrait orientation. A covering 36 is used to protect the connection between the wire and the link, and prohibit damage to the inside of the conduit 18.

Figure 3F:
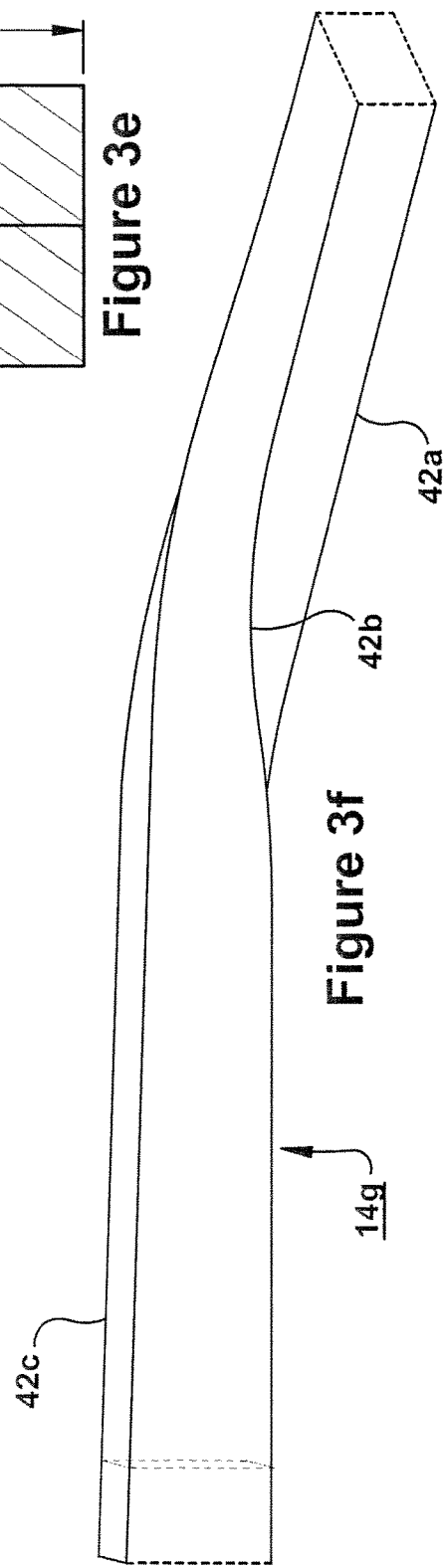
FIG. 3f is an enlarged perspective view of the designated circular area of FIG. 3.

The most distal portions of the loop 12 is illustrated in FIGS. 3d and 3f In the exemplary loop 12, the wire twists on each side of the loop near the distal tip 40 of tool. Referring now to FIG. 3f, an enlarged version of one twisted portion is shown. Within the illustrated area, the wire twists and turns similar to the wire within a transitional portion 14g. For discussion purposes, the wire 14 is discussed herein as traveling in the direction toward the distal tip 40. Within the illustrated portion 14g, an entering portion 42a of the wire has a width greater than a height, in other words, the rectangular shape of the wire is in a landscape orientation. The inward side of the wire twists at a middle portion 42b upward along an axis of the wire, and the wire itself bends outward away from the longitudinal axis of the loop 12. As such, an exiting portion 42c of the wire 14a has height greater than a width, and the rectangular shape of the wire is in a portrait orientation. The wire continues toward the distal tip 40 to form a torsion tip having a 360° loop.

Figure 3G:
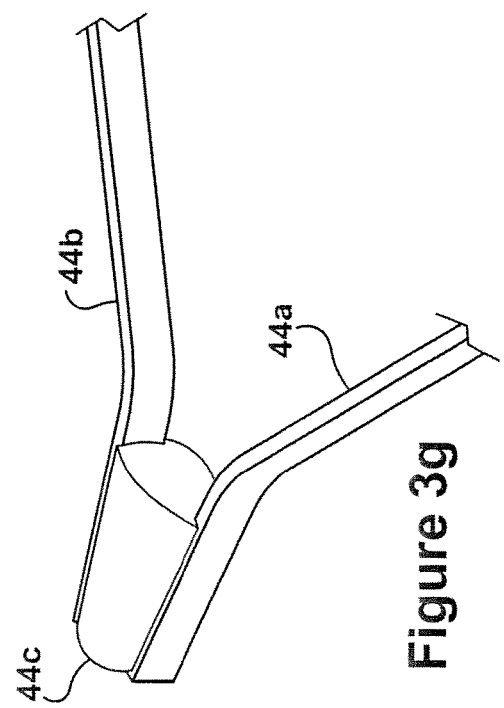
FIG. 3g is an enlarged view of another snare having another distal end.

The distal tip 40 of the tool may have alternative shapes. The wire may form a torsion tip with a 180° bend, as shown in the exemplary loop of FIG. 4. In another distal tip, the wire within the 180° bend may be in a landscape orientation, as shown in the exemplary loop of FIG. 5. Still another distal tip is shown in the enlarged view of FIG. 3g. In this exemplary distal tip, the loop is formed by a wire having two portions 44a, 44b. The two wire portions are held together by a ball tip 44c at a distal most point. As assembled, the wire portions function as a loop the same as discussed herein.

Figure 4:
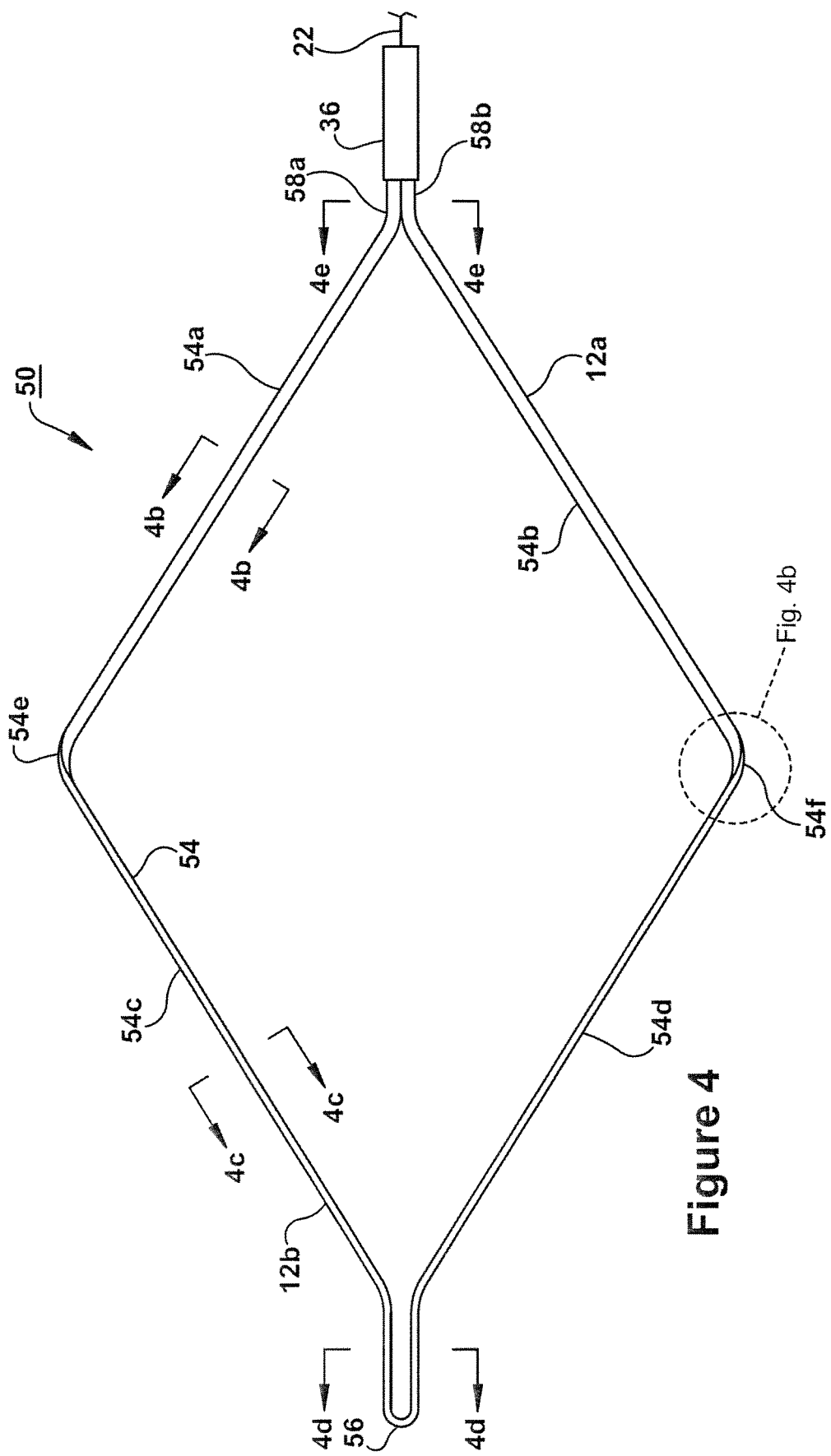
FIG. 4 is a top view of another snare, showing the snare in a deployed position.

A tool of the invention may have a loop having a variety of shapes, and a wire in more than one orientation. Other embodiments of the invention will now be discussed. FIG. 4 is a top view of a loop, showing the loop in a deployed position. The loop 50 is in a polygon-shape, and specifically, is in a diamond shape. That is to say, the loop has the same general orientation about a longitudinal axis and a lateral axis $A_2$ as the loop illustrated in FIG. 3. Thus, the loop 50 has a proximal portion 12a and a distal portion 12b which are essentially the same in size.

As discussed herein, the wire 54 orientation in FIG. 4 is generally reversed as compared to the wire orientation in FIG. 3. As shown in FIG. 4, a transitional portion 54e, 54f on either side of the loop 54 is disposed between the proximal portion 12a and the distal portion 12b. An enlarged perspective view of the transitional portion 54f is illustrated in FIG. 4a. Within the transitional area 54f, the wire twists and turns. For discussion purposes, the wire 54 is discussed herein as traveling for the proximal portion 12a to the distal portion 12b. Within the transitional portion 54f, an entering portion 52a of the wire has a width greater than a height, in other words, the rectangular shape of the wire is in a landscape orientation. The bottom of the wire twists at a middle portion 52b outward along an axis of the wire, and the wire itself bends inward toward the longitudinal axis of the loop 50. In exemplary transitional portion 54f shown, the wire is twisted about 90°. As such, an exiting portion 52c of the wire 54 has height greater than a width, and the rectangular shape of the wire is in a portrait orientation.

As discussed herein, the proximal portion and the distal portion are each formed from a wire 54. The wire is orientated in the proximal portion in a different orientation than in the distal portion. In the exemplary loop 50 shown in FIG. 4, the wire 54 has a rectangular-shaped cross section. The cross-sectional shape of the wire 54, relative to a horizontal plane during application, varies at different locations of the loop, as shown at different locations of the loop in FIGS. 4a-4e. As discussed herein, the cross-sectional shape of the loop in the proximal portion relative to the cross-sectional shape of the loop in the distal portion contributes to the advantageous features on the tool 10.

FIG. 4b is sectional view of the wire in the proximal portion 12a of the loop 50, and shown along the line 4b-4b of FIG. 4. The wire has a width $W_2$ which is greater than the height $H_2$. With the wire in an opposite orientation, FIG. 4c is sectional view of the wire in the distal portion of the loop 12. The wire is shown along the line 4c-4c of FIG. 4. The wire has a height $H_1$ which is greater than the width $W_1$. As such, the piece of wire having a cross-sectional width $W_2$ in the proximal portion equal to a cross-sectional height $H_1$ in the distal portion and unequal to a cross-sectional width in the distal portion $W_1$.

Other sections of the loop compare similarly to FIGS. 3b-3e. In the cross-section show in FIG. 4e, the wire portions 58a, 58b in the most proximal part of the loop as shown. The wire portions are connected to the link 22. As shown in FIG. 4 and in the cross-sectional view in FIG. 4e, the two end portions 58a, 58b are contiguous and each in a landscape orientation. The most distal portion of the loop 12 is illustrated in FIG. 4d. In the exemplary loop 50, the wire bends outward on each side of the loop near the distal tip 56 of tool. The wire continues toward the distal tip 56 to form a torsion tip having a 180° loop, and the wire in a portrait orientation.

Figure 5:
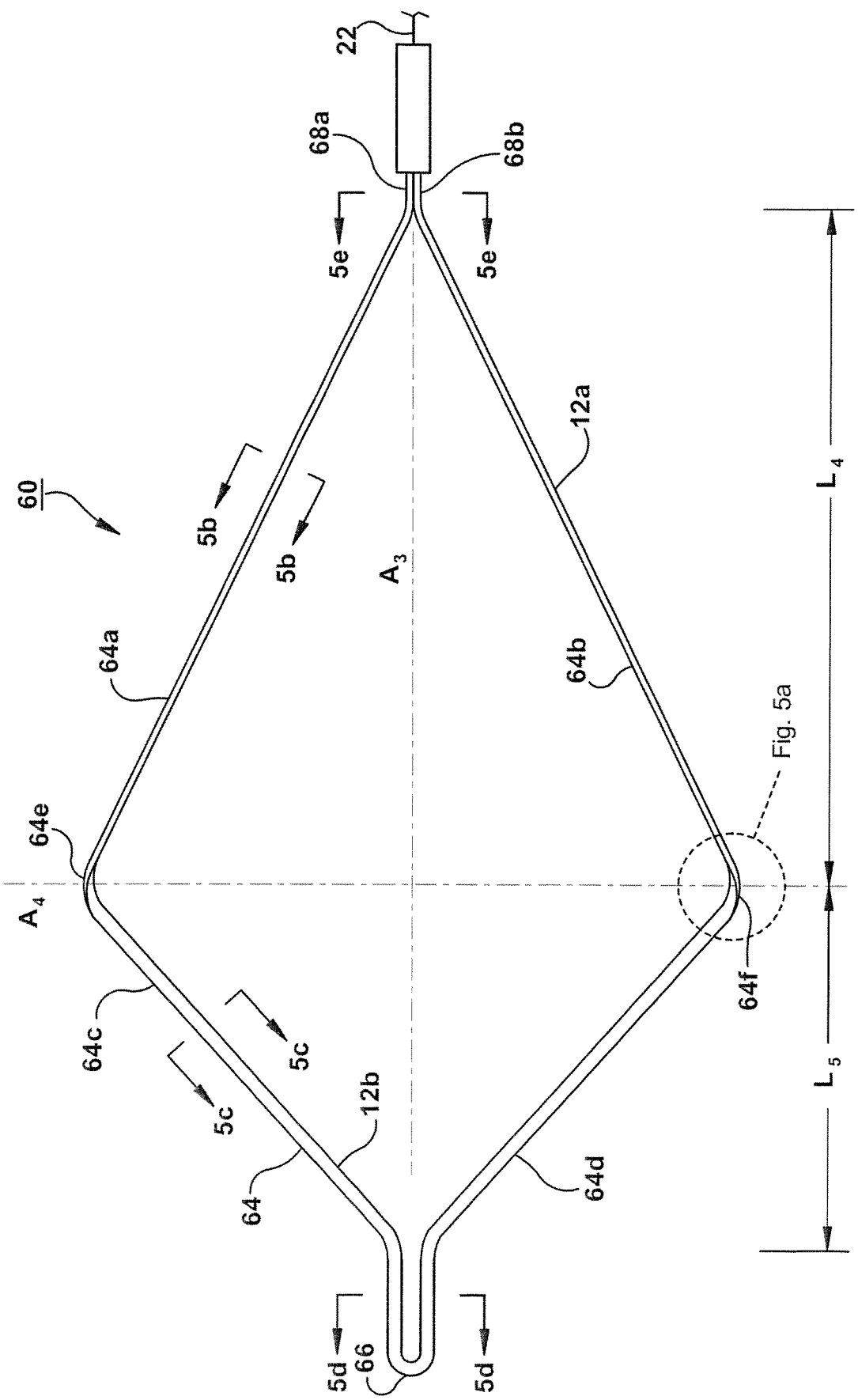
FIG. 5 is a top view of another snare, showing the snare in a deployed position.
Figure 6:
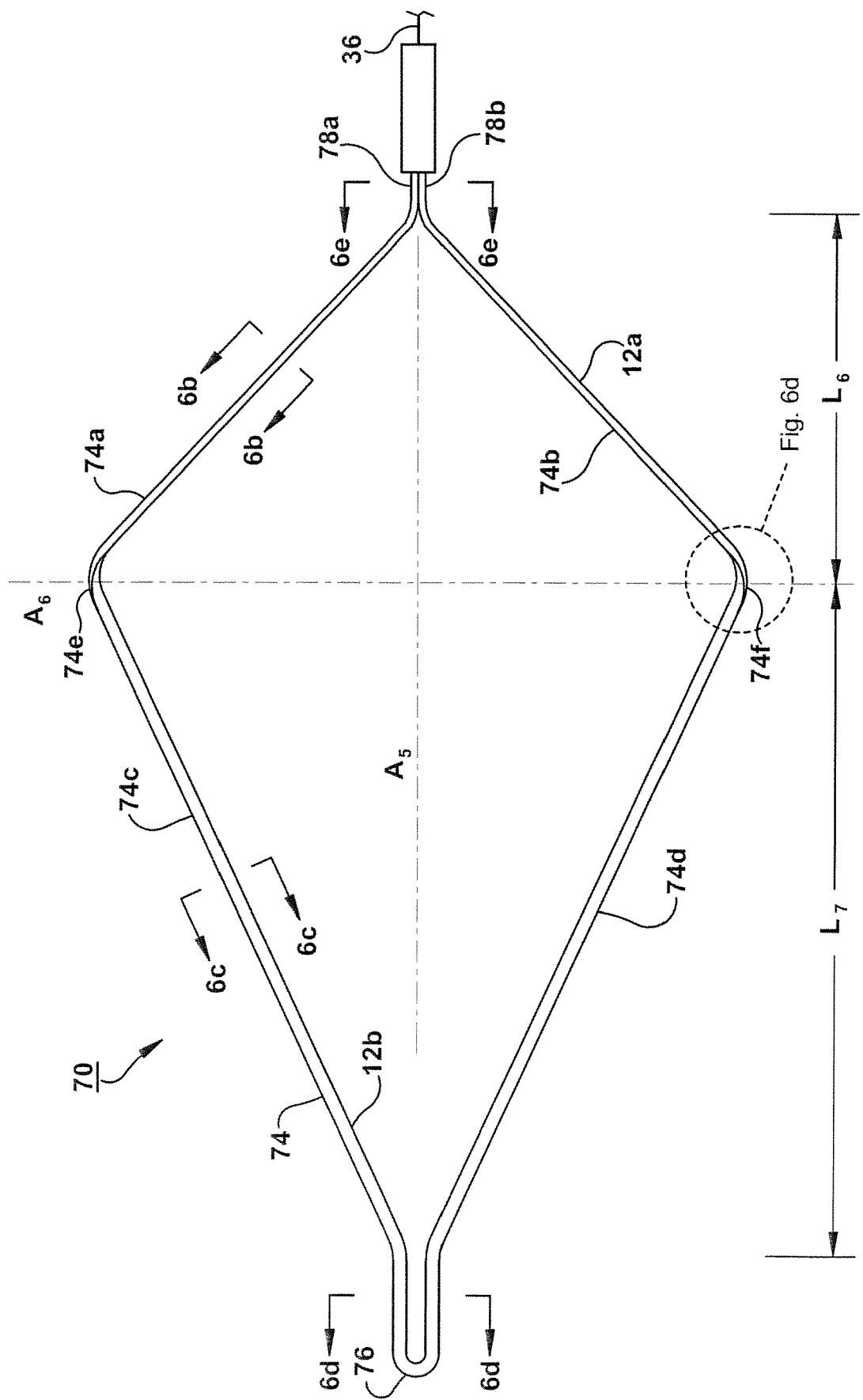
FIG. 6 is a top view of another snare, showing the snare in a deployed position.
Figure 7:
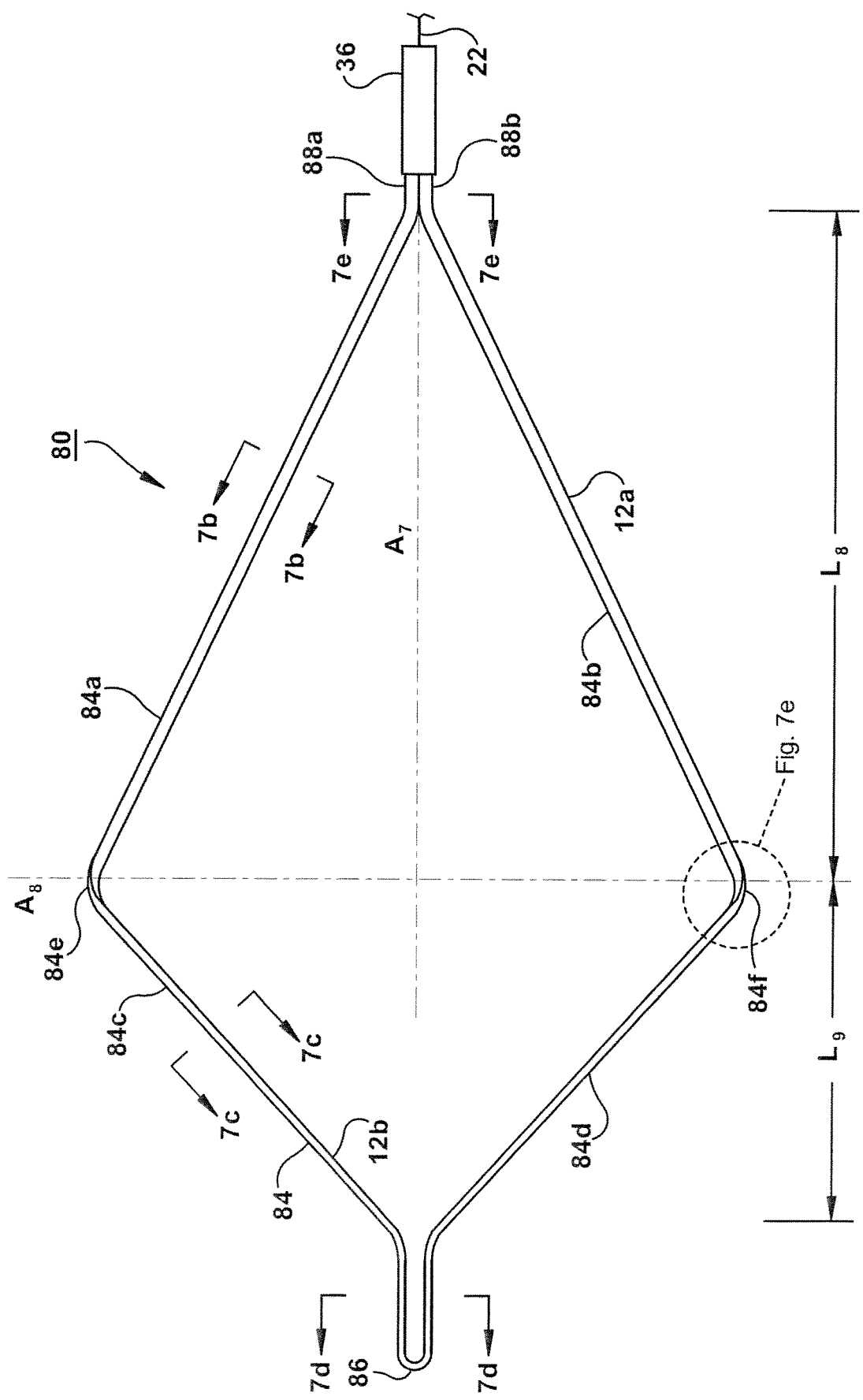
FIG. 7 is a top view of another snare, showing the snare in a deployed position.
Figure 8:
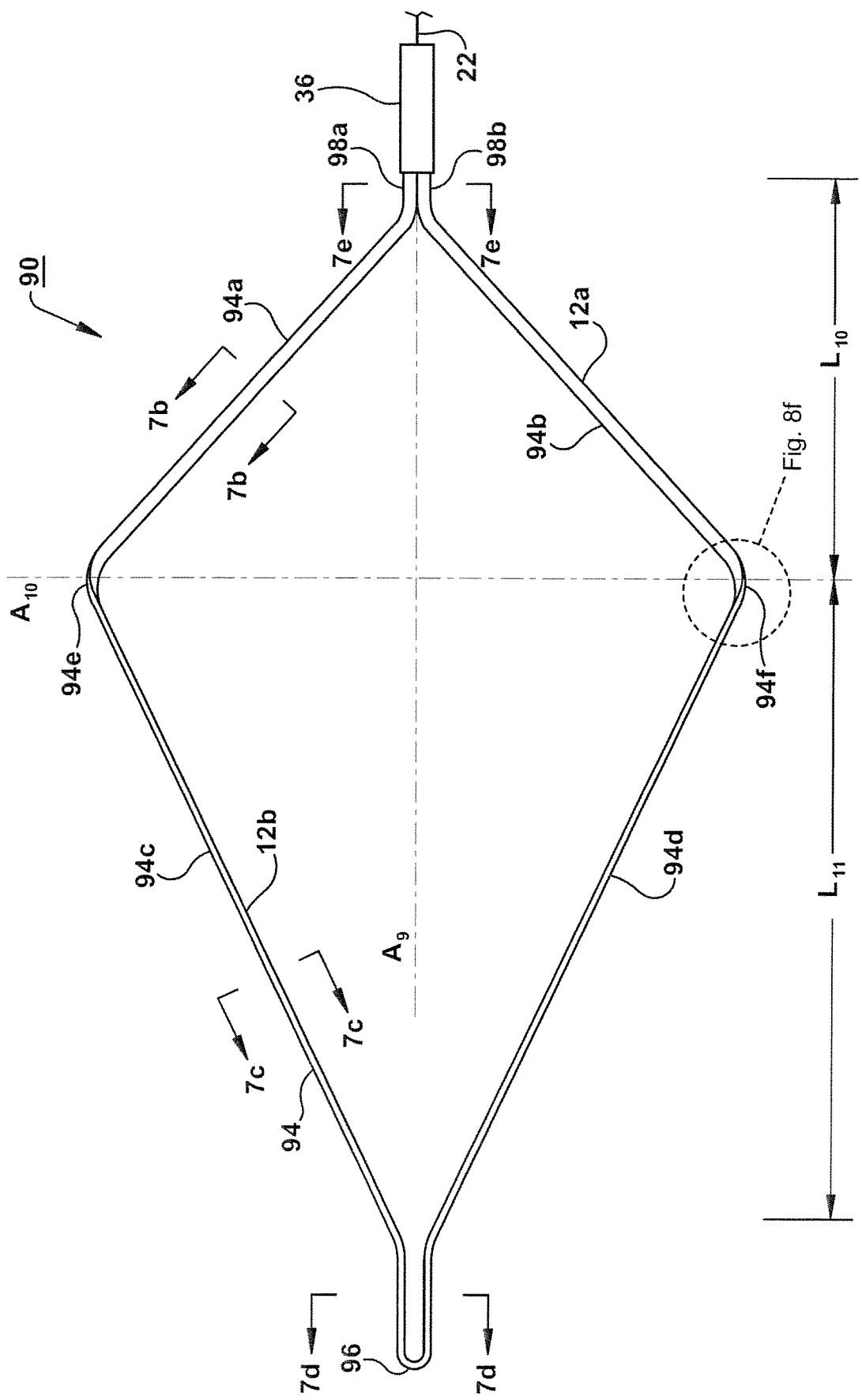
FIG. 8 is a top view of another snare, showing the snare in a deployed position.

The invention may be practiced with a loop in which the proximal portion and the distal portion are not the same size. FIGS. 5-8e shown four exemplary loops in which the proximal portion is not the same size as the distal portion. For example, FIGS. 5 and 7 show a proximal portion in which the proximal portion is larger than the distal portion, and FIGS. 6 and 8 show a proximal portion which is smaller than the distal portion. In these embodiments, all the loops are symmetric about a longitudinal axis of the link. In two of the loops, FIGS. 5 and 6, the wire is in a portrait orientation in the proximal portion, and in a landscape portion in the distal end. In the other two loops, FIGS. 7 and 8, the wire is in a landscape orientation in the proximal portion, and in a portrait orientation in the distal end. Each of these exemplary loops will now be discussed in some detail. However, properties of each loop can be identified by one with skill in the art by other discussions herein and by the Figures.

The loops illustrated in FIGS. 5, 6, 7 and 8 are kite-shaped. In FIG. 5, the loop 60 is shaped and arranged such that a proximal portion 12a has a length $L_4$ which is greater than a length $L_5$ of the distal portion 12b. Similarly, the loop 80 shown in FIG. 7 is shaped and arranged such that a proximal portion 12a has a length $L_8$ which is greater than a length $L_9$ of the distal portion 12b. FIGS. 6 and 8 illustrate loops that have the same shape, but are arranged in a different orientation. In FIG. 6, the loop 70 is shaped and arranged such that a proximal portion 12a has a length $L_6$ which is less than a length $L_7$ of the distal portion 12b. Similarly, the loop 90 shown in FIG. 8 is shaped and arranged such that a proximal portion 12a has a length $L_{10}$ which is less than a length $L_{11}$ of the distal portion 12b.

The loops illustrated in FIGS. 5, 6, 7 and 8 also vary in the orientation of the wire. The loop 60 of FIG. 5 and the loop 70 of FIG. 6 have a wire 64, 74, respectively, in which the wire in the proximal portion has a height greater than a width, that is to say, is rectangular shaped and in the portrait orientation. The wire 64, 74, respectively, in the distal portion has a width greater than a height, that is to say, is rectangular shaped and in the landscape orientation. The wires of the loops 80, 90, respectively, in FIGS. 7 and 8 are in the opposite direction. The FIGS. 5a-5e, 6a-6e, 7a-7e and 8a-8e, with reference characters relating to FIGS. 5, 6, 7 and 8, show the wire 64, 74, 84, 94, respectively, at various points along the loop, 60, 70, 80, 90, respectively, and clearly illustrated wire shape, wire orientation, wire twists, and wire bends. It should be apparent to one with skill in the art, that the loop embodiments illustrated in FIGS. 5-8e are for exemplary purposes only, and other loop shapes and arrangements may be used in the practice of this invention.

Figure 9A:
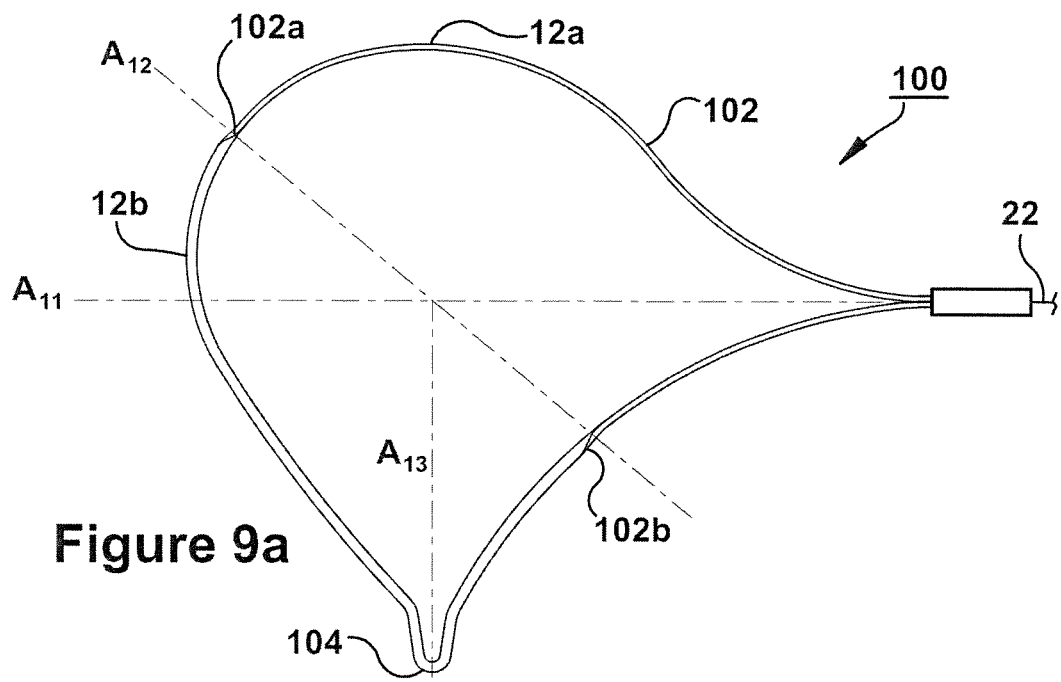
FIG. 9a is a top view of another snare having an irregular shape.

A loop may have an irregular shape in the practice of this invention. For example, FIG. 9a is a top view of another tool having an irregular shaped loop. The loop 100 is asymmetric about a longitudinal axis $A_{11}$ and is asymmetric about a lateral axis $A_{12}$. The proximal portion 12a and the distal portion 12b are defined by two transitional points 102a, 102b, in which the wire twists from a portrait orientation in the proximal portion 12a to a landscape orientation in the distal portion 12b. A longitudinal axis $A_{13}$ of the distal end 104 is essentially perpendicular to the longitudinal axis $A_{11}$ of the link 22.

Figure 9B:
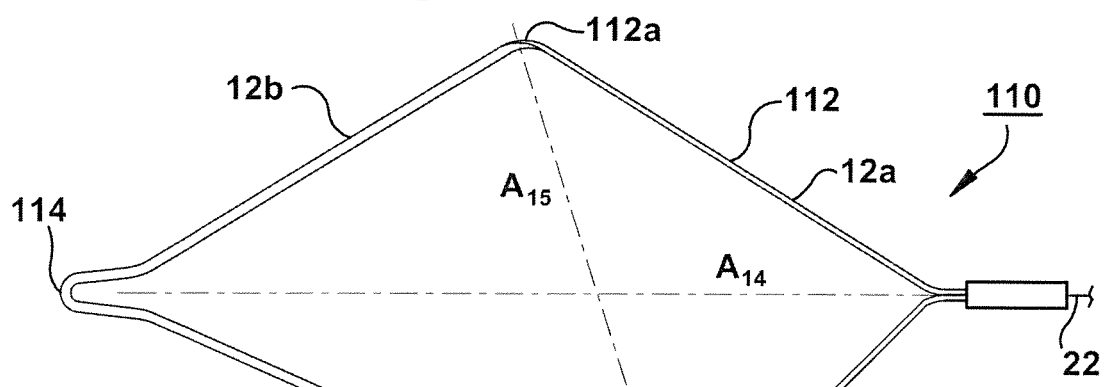
FIG. 9b is a top view of another snare having an irregular shape.

Another exemplary loop having an irregular shape is shown in FIG. 9b. The loop 110 is symmetric about a longitudinal axis $A_{14}$ and is asymmetric about a lateral axis $A_{15}$. In this exemplary loop, the proximal portion 12a and the distal portion 12b are not divided by an axis which is perpendicular to the longitudinal axis of the link 22. The proximal portion 12a and the distal portion 12b are defined by two transitional points 112a, 112b, in which the wire twists from a portrait orientation in the proximal portion 12a to a landscape orientation in the distal portion 12b. The distal end 114 is formed by a less than 180° bend of the wire in a landscape orientation.

Figure 9C:
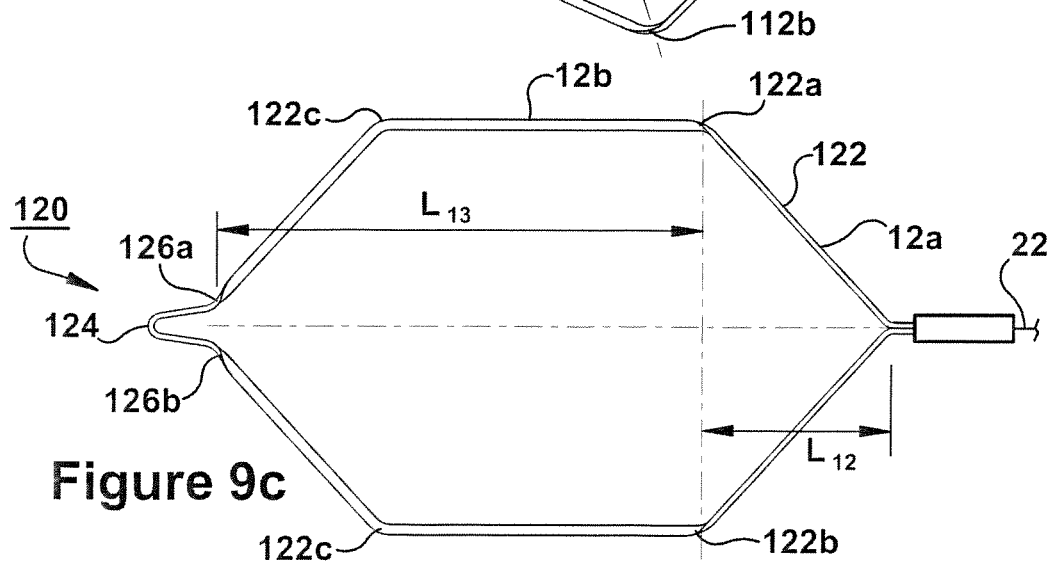
FIG. 9c is a top view of another snare having a hexagon shape.

Another loop which is polygon-shaped is illustrated in FIG. 9c. The loop 120 is hexagon-shaped and is symmetric about a longitudinal axis $A_{16}$, but is asymmetric about a lateral axis $A_{17}$. The proximal portion 12a and the distal portion 12b are defined by two transitional points 122a, 122b, in which the wire 122 twists from a portrait orientation in the proximal portion 12a to a landscape orientation in the distal portion 12b. However, the wire maintains a landscape orientation as it bends inwards at two other points 122c, 122d along the hexagon shape. With the loop 120 in this arrangement, the proximal portion and the distal portion are not the same length. Specifically, the proximal portion 12a has length $L_{12}$ which is shorter than the length $L_{13}$ of the distal portion 12b.

The distal portion of the hexagon-shaped loop 120 has similar properties to the loop illustrated in FIG. 3. At two transitional points 126a, 126b, the wire 122 twists from a landscape orientation to a portrait orientation. In this portrait orientation, the distal end 124 of the loop 120 is formed by a less than 180° bend of the wire 122.

Figure 9D:
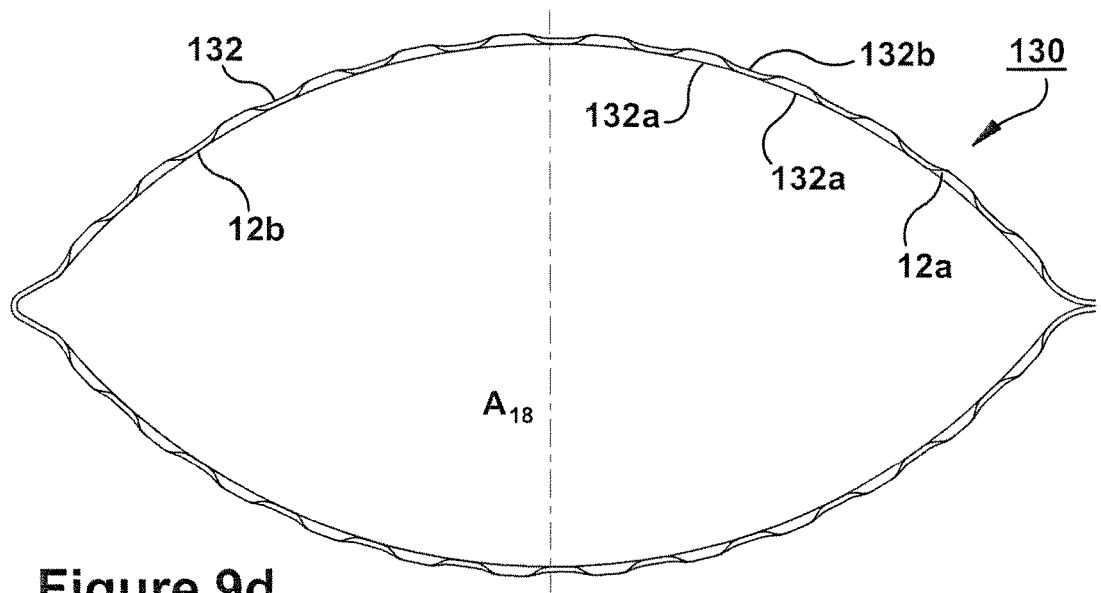
FIG. 9d is a top view of another snare having an oval-shape.
Figure 9E:
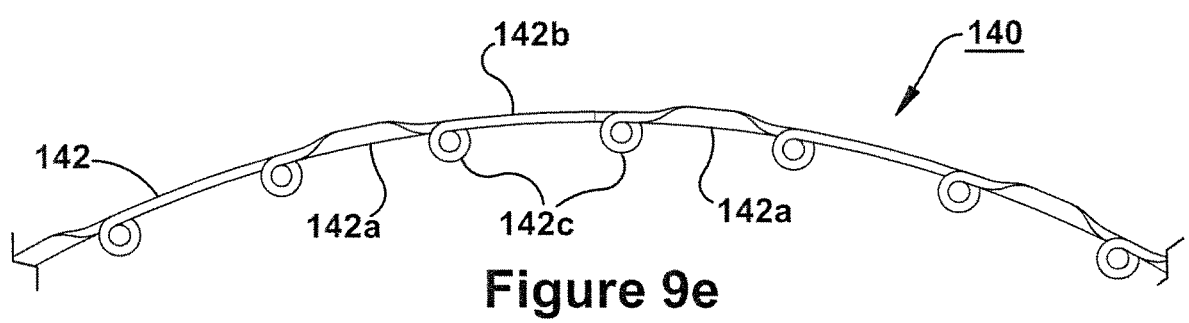
FIG. 9e is a top view of another snare having an oval-shape.

Referring now to FIGS. 9d and 9e, two oval-shaped loops are shown. In FIG. 9d, an oval-shaped loop 130 has a wire 132 which includes a pattern of wire segments. The pattern is an alternating series of wire segments between a portrait orientation and a landscape orientation. The portrait orientation segments 132b and the landscape orientation segments 132a may be of different lengths, or may be of the same length, such as for example, 3 mm. A lateral axis $A_{18}$ defines, or separates, the loop 130 into a proximal portion 12a and a distal portion 12b.

FIG. 9e shows an enlarged view of a wire having similar properties as the wire 132 of FIG. 9d. The wire 142 illustrated in FIG. 9e also is used to form an oval-shaped loop which includes a pattern on wire segments. The pattern is an alternating series of wire segments between a portrait orientation and a landscape orientation. The portrait orientation segments 142b and the landscape orientation segments 142a may be of different lengths, or may be of the same length, such as for example, 3 mm. The segments 142a, 142b are separated by a 360° loop 142c. The wire 142 is in the portrait orientation within each loop 142c, but the loop may be made in the landscape orientation.

The wires 132, 142 on FIGS. 9d and 9e, respectively, may be used to construct a loop with advantageous properties. A loop constructed of either wire 132, 142 has a proximal portion and a distal portion, and each portion has segments in the portrait orientation and segments in the landscape orientation. As discussed herein, each particular orientation offers advantageous properties. Thus, the number and length of each particular segment type in the proximal portion and in the distal portion can be specified to produce desired performance characteristics of the tool.

Figure 9F:
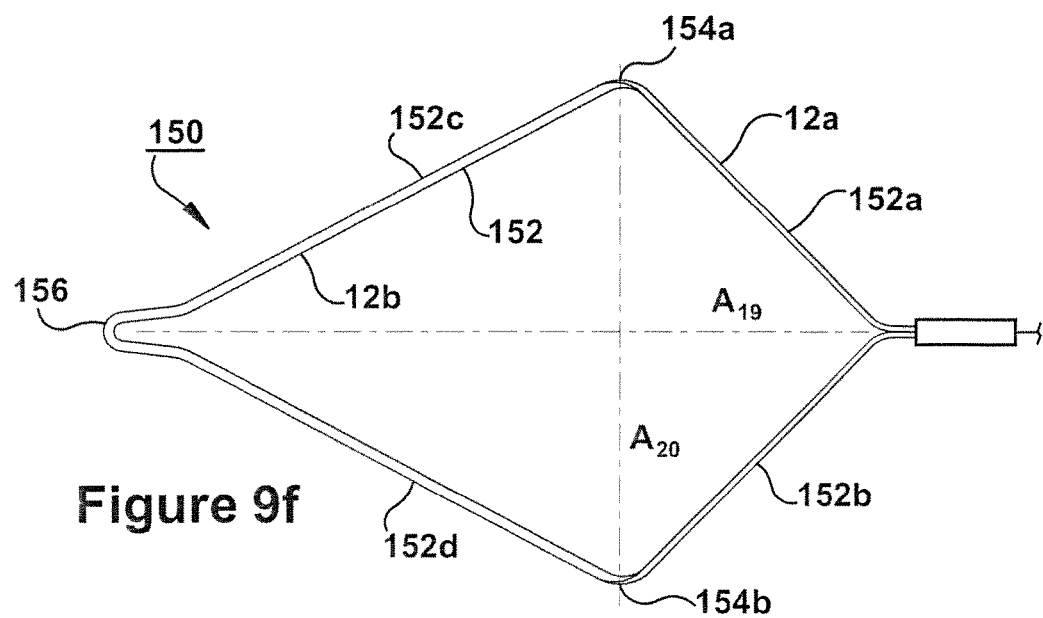
FIG. 9f is a top view of another snare having an irregular shape.

Another loop having an irregular shape is shown in FIG. 9f. This loop 150 is generally arrowhead-shaped. The loop 150 is divided into a proximal portion 12a and a distal portion 12b by two transitional portions 154a, 154b. The wire 152 is in a portrait orientation in the proximal portion 12a and in a landscape orientation in the distal portion 12b. At the distal end 156 of the loop 150, the wire 152 maintains a landscape orientation. The distal end 156 is formed by a less than 180° bend of the wire 152.

In the practice of this invention, a loop which is arrowhead-shaped may be polygon-shaped, or the loop may have curved portions. The loop 150 illustrated in FIG. 9f is polygon-shaped, and is symmetric about the longitudinal axis $A_{19}$ and the lateral axis $A_{20}$.

As discussed herein, the wire used to form a loop of this invention may be of different types of materials, and may be made by different manufacturing methods. Also, the wire may be of different cross-sectional shapes. Referring to FIGS. 3 and 3b, the exemplary wire 14 has a rectangular cross-section. Three other exemplary types of cross-sections are shown in FIGS. 10a-12d. These three wire types, as well as wires having a cross-section not shown, may be used with any loop shape discussed herein.

Referring now to FIGS. 10a-10d, a wire 200 with a diamond-shaped cross-section is illustrated. In FIGS. 10b and 10c, the wire 200 is shown in a portrait orientation and in a landscape orientation, respectively. A distal end having a 360° bend formed from the wire 200 is shown in FIG. 10d. A transitional portion of the wire 200 is shown in FIG. 10a. In the transition portion, the wire 200 has an entering portion 202a in a portrait orientation, a center portion 202b in which the wire bends inward and twists °90, and an exiting portion 202c in a landscape orientation.

Referring now to FIGS. 11a-11d, a wire 210 with an oval-shaped cross-section is illustrated. In FIGS. 11b and 11c, the wire 210 is shown in a portrait orientation and in a landscape orientation, respectively. A distal end having a 360° bend formed from the wire 210 is shown in FIG. 10d. A transitional portion of the wire 210 is shown in FIG. 11a. In the transition portion, the wire 210 has an entering portion 212a in a portrait orientation, a center portion 212b in which the wire bends inward and twists °90, and an exiting portion 212c in a landscape orientation.

The wire shown in FIGS. 12a-12d has a square-shaped cross-section. In other words, the wire 220 has a height $H_1$ which is equal to the width $W_1$, as shown in FIG. 12b. Because the wire has a square-shaped cross-section, the height of the wire is always equal to the width, at any particular orientation, such as for example, at an orientation turned 0° relative an application surface, such as shown in FIG. 12b, or at an orientation turned 45° relative an application surface, such as shown in FIG. 12c. A transitional portion of the wire 220 is shown in FIG. 12a. In the transition portion, the wire 220 has an entering portion 212a in an orientation turned 0° relative an application surface, a center portion 212b in which the wire bends inward and twists °45, and an exiting portion 212c in an orientation turned 45° relative an application surface.

A method of use of the device 10 for removing a polyp from a gastro-intestinal wall of a patient will now be discussed. The FIGS. 13-19 illustrate an exemplary method for removal and recovery of a polyp. It should be understood by others with skill in the art than other removal methods can be undertaken in the practice of the invention.

Figure 13:
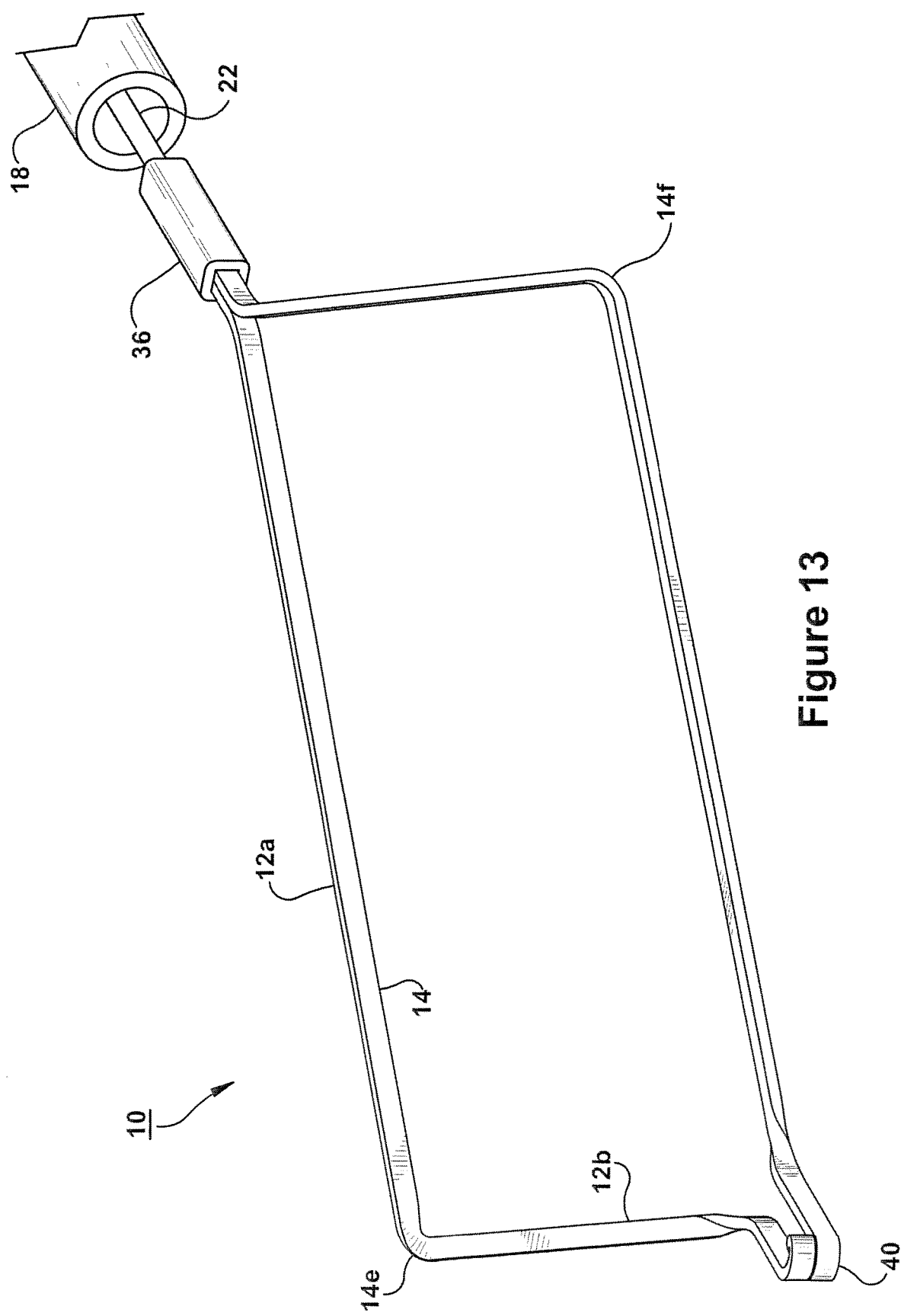
FIG. 13 is a perspective view of the snare of FIG. 3, showing the snare in a deployed position.
Figure 14:
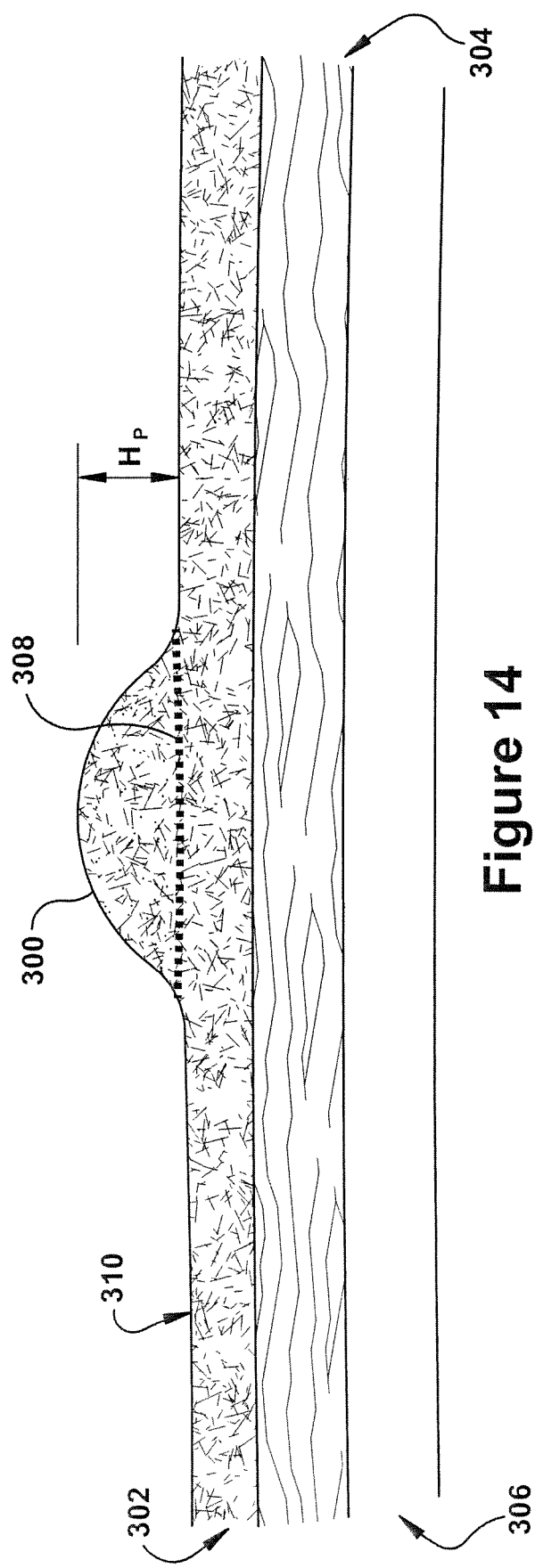
FIG. 14 is a side view of a polyp on the mucosa layer of an intestinal wall.

Referring to FIG. 13, a perspective view of the tool 10 of FIG. 3 is shown with the loop in a deployed position. In this deployed position, or in another position, the tool 10 may be placed adjacent or around a targeted tissue. FIG. 14 shows a side view of a polyp 300 on an intestinal wall. Specifically, the polyp is formed on the mucosa layer 302, above the submucosa layer 304 and muscularis 306. The polyp is shown at a relaxed height Hp above the top surface 310 of the mucosa layer 302. As discussed herein, a polyp may be difficult to remove by cutting, especially along a target cut line on the first attempt. Further complicating such a procedure, a polyp may grow back if not transected at its base. In the exemplary method illustrated, the polyp may be cut along a target cut line 308, which may be at a level even with the top surface 310 of the mucosa layer 302.

Figure 15:
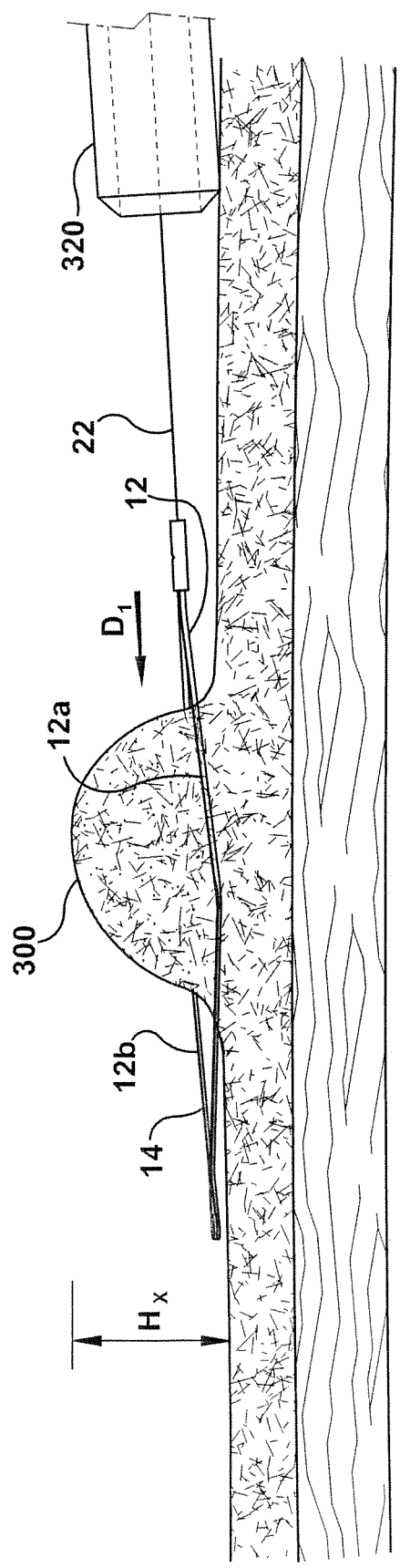
FIG. 15 is a side view of the snare device of FIG. 3 positioned around the polyp of FIG. 14, showing the snare in a position while in motion toward deployment.
Figure 16:
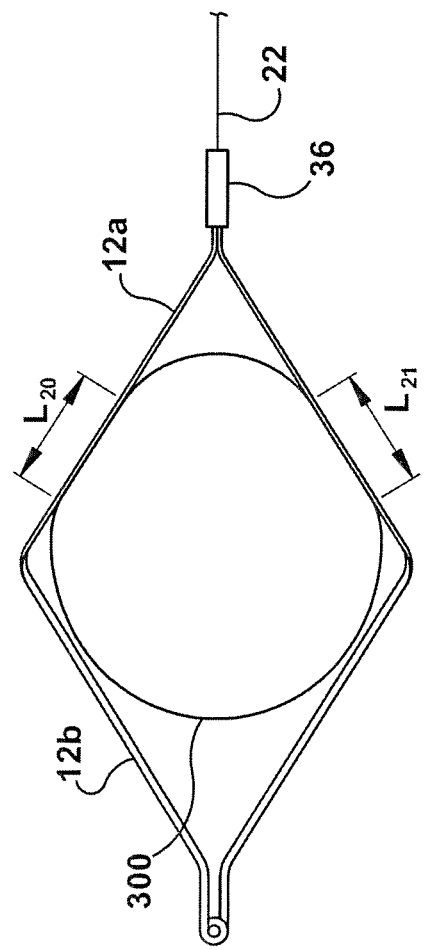
FIG. 16 is a top view of FIG. 15.

Referring now to FIG. 15, an intubated endoscope 320 is shown adjacent the mucosa layer 302. The distal portion of the tool 10 of FIG. 13 is shown extending from an instrument channel of the endoscope to a location surrounding the polyp 300. The conduit 18 is not shown for clarity. The loop 12 is shown in a deployed position after movement in a deployment direction $D_1$. As a consequence of the deployment, the polyp 300 is manipulated by the proximal portion 12a of the loop 12. As discussed with reference to FIG. 3, the proximal portion is formed by a wire having a rectangular-shaped cross-section and in a portrait orientation. As such, the wire 12 contacts the polyp in a plowing effect to pinch and raise the polyp relative the top surface 310 of the mucosa layer 302. In a top view in FIG. 16, the wire is shown contacting the polyp along two lengths $L_{20}$, $L_{21}$ of the proximal portion.

Referring again to FIG. 15, the plowing technique has the advantageous effect of pre-conditioning the polyp 300 for removal along the target cut line 308. The polyp 300 is raised to a pre-conditioned height $H_x$ in which a higher percentage of the mass of the polyp is above the target cut line 308, and the center of gravity of the polyp 300 has been raised, each relative to the relaxed polyp condition shown in FIG. 14. The plowing also raised the amount of the polyp which is about the cutting face of the distal portion.

Figure 17:
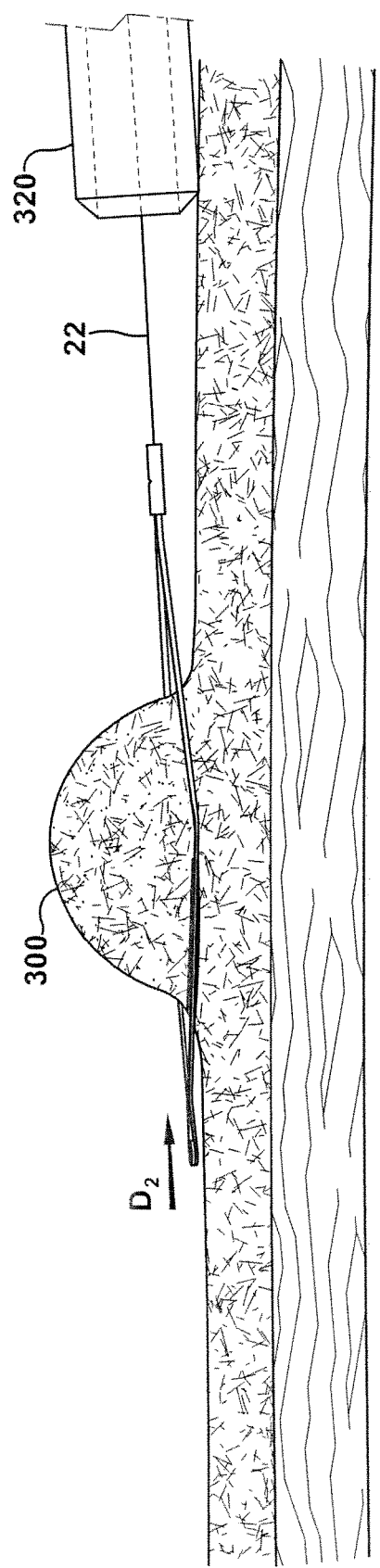
FIG. 17 is a side view of the snare device of FIG. 3 positioned around the polyp of FIG. 14, showing the snare in a position while in motion toward retrieval.
Figure 18:
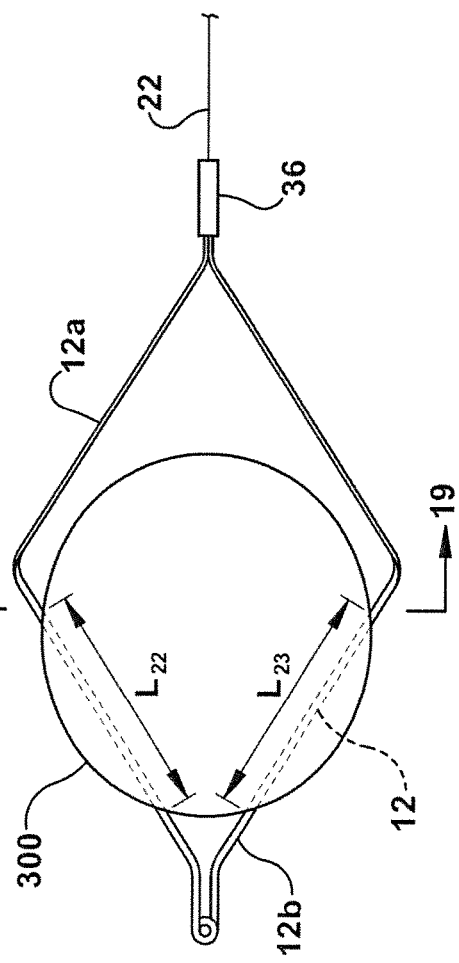
FIG. 18 is a top view of FIG. 17.
Figure 19:
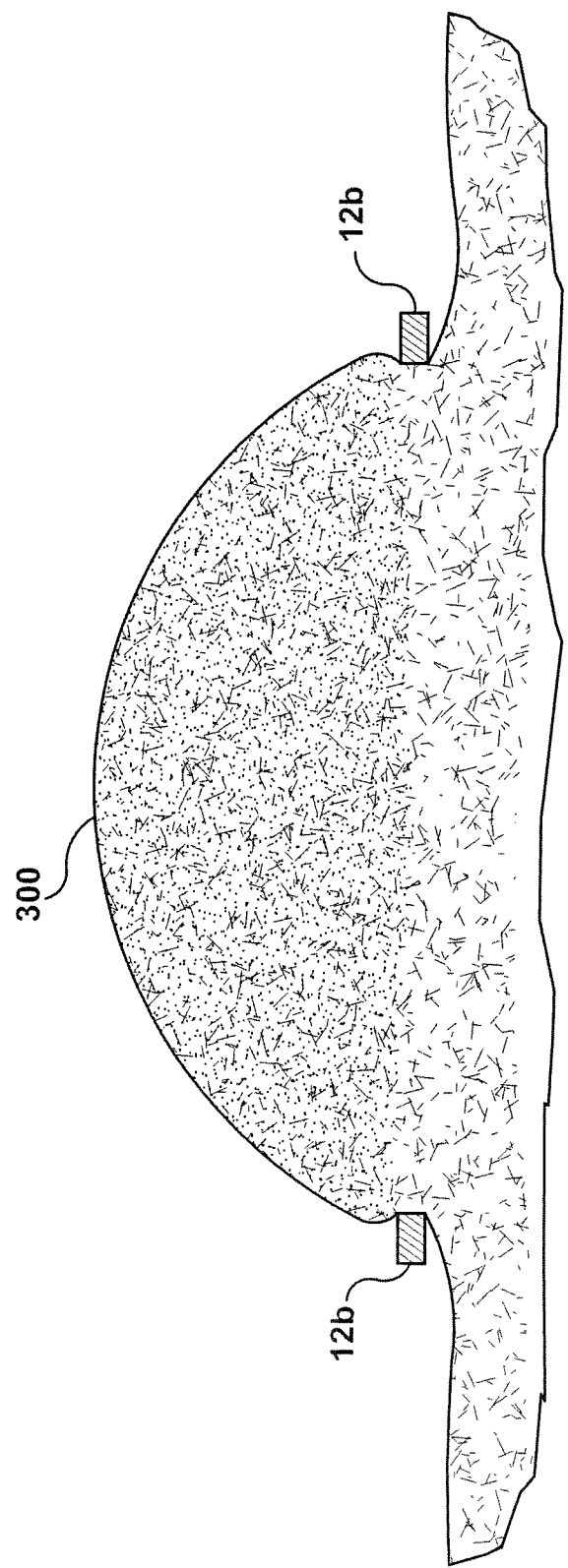
FIG. 19 is an enlarged sectional view of the snare of FIG. 3, shown along the line 19-19 of FIG. 18.

While the polyp is in the pre-conditioned position, the loop is manipulated in a retrieval direction $D_2$. As a consequence of the retrieval, the cutting edge of the distal portion 12b of the loop 12 cuts into the polyp 300 at or near the target cut line 308. As discussed with reference to FIG. 3, the distal portion is formed by a wire having a rectangular-shaped cross-section and in a landscape orientation. As such, the wire 12 contacts the polyp in a cutting effect to cut into the polyp as shown in FIG. 17. In a top view in FIG. 18, the wire is shown at a position during the cutting procedure with the distal portion contacting the polyp along two lengths $L_{22}$, $L_{23}$. FIG. 19 shows an enlarged sectional view of the polyp along the line 19-19 of FIG. 18. As discussed, it should be apparent to one skilled in the art that other methods of use of the inventive tool are possible other than the exemplary method shown and discussed.

Figure 20:
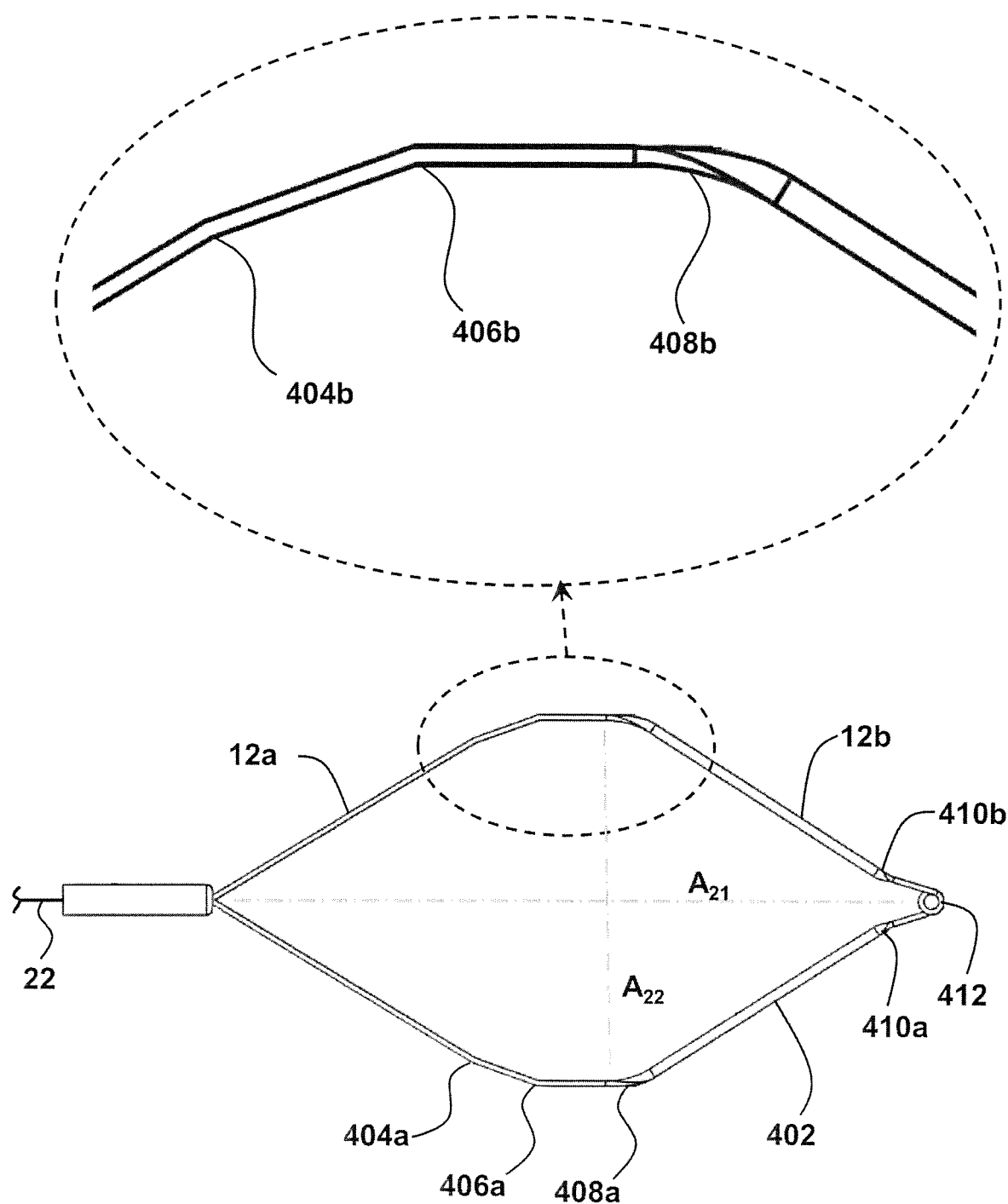
FIG. 20 is a top view another snare having an irregular shape.

One more loop, which is polygon-shaped, is illustrated in FIG. 20. The loop 400 is symmetric about a longitudinal axis $A_{21}$, but is asymmetric about a lateral axis $A_{22}$. The wire 402 of the loop 400 includes, at its proximal portion 12a, a first pair inward bends 404a, 404b, followed distally by a second pair of inward bends 406a, 406b. The wire 402 maintains a landscape orientation as it bends inwards at points 404a, 404b, 406a and 406b. These additional bends (i.e., memory points) may help the loop 400 resist collapse and retain its shape over time. The proximal portion 12a and the distal portion 12b of the loop 400 are defined by two transitional points 408a, 408b, in which the wire 402 twists from a portrait orientation in the proximal portion 12a to a landscape orientation in the distal portion 12b.

The distal portion of the loop 400 has similar properties to the loop illustrated in FIG. 3. At two transitional points 410a, 410b, the wire 402 twists from a landscape orientation to a portrait orientation. In this portrait orientation, the distal end 412 of the loop 400 includes a torsion tip having a 360° loop. While the loop 400 includes two bends in the proximal portion 12a, other embodiments may include more bends in the proximal portion 12a, distal portion 12b, or both. Further, the addition of collapse-resistant bends may be used in conjunction within any other of the previously described embodiments. For example, a loop with at least two proximal bends may have an oval, arrowhead, diamond or kite shape (ignoring small variations from the proximal bends), may have wire with an oval or diamond cross-section, etc.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, circuits, devices and components, alternatives as to form, fit and function, and so on) may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A tissue removal tool for use with an endoscope, the tool comprising:
a loop formed by a piece of wire and movable between an open position and a closed position;
wherein the shape of the loop is defined in the open position by a proximal portion and a distal portion, the distal portion having a cross-sectional height substantially defined by a substantially planar surface, the proximal portion having a cross-sectional width at least partially defined by the substantially planar surface, the proximal portion and the distal portion being separated by a transitional portion, wherein the piece of wire in the transitional portion is twisted along an elongate axis of the piece of wire by at least 45 degrees on at least one side of the loop so that the proximal portion pushes against a piece of tissue being removed to raise the piece of tissue and pinches the piece of tissue, and the distal portion transects the piece of tissue after the proximal portion pinches the piece of tissue; and
wherein the proximal portion comprises at least two collapse-resistant bends on at least one side of the loop.

2. The tissue removal tool of claim 1 wherein the piece of wire is twisted in the transitional portion by essentially 90 degrees on at least one side of the loop.

3. The tissue removal tool of claim 1 wherein the loop comprises a torsion spring tip at a distal end thereof.

4. The tissue removal tool of claim 1 wherein the loop is essentially oval-shaped in the open position.

5. The tissue removal tool of claim 1 wherein the loop is essentially arrowhead-shaped in the open position.

6. The tissue removal tool of claim 1 wherein the loop is essentially polygon-shaped in the open position.

7. The tissue removal tool of claim 1 wherein the loop is essentially diamond-shaped in the open position.

8. The tissue removal tool of claim 1 wherein the loop is essentially kite-shaped in the open position.

9. The tissue removal tool of claim 1 wherein a length of the proximal portion is longer than a length of the distal portion.

10. The tissue removal tool of claim 1 wherein a length of the proximal portion is shorter than a length of the distal portion.

11. The tissue removal tool of claim 1 wherein the piece of wire is rectangle-shaped in cross-section.

12. The tissue removal tool of claim 1 wherein the piece of wire is oval-shaped in cross-section.

13. The tissue removal tool of claim 1 wherein the piece of wire is diamond-shaped in cross-section.

14. The tissue removal tool of claim 1 wherein the piece of wire is square-shaped in cross-section.

15. A snare for use with an endoscope, the snare comprising:
a support assembly having a base and an elongated hollow tube;
a transmitting assembly having a handle movable relative to the base and a link having a first end fixed to the handle and a second end remote from the base, the link extending substantially through a length of the tube; and
a loop formed by a piece of wire and attached to the link, and the loop being movable between an expanded position and a collapsed position by action of the handle relative to the base;
wherein the loop is formed by a proximal portion, a distal portion, and a transitional portion separating the proximal portion and the distal portion, wherein the loop is defined by a single twist that extends substantially along an elongate axis of the wire by at least 45 degrees on each side of the transitional portion; and
wherein the proximal portion comprises at least two collapse-resistant bends on at least one side of the loop.

16. The snare of claim 15 wherein the piece of wire has a cross-sectional height larger than a cross-sectional width in the proximal portion and a cross-sectional width larger than a cross-sectional height in the distal portion.

17. The snare of claim 15 wherein the piece of wire has a cross-sectional height smaller than a cross-sectional width in the proximal portion and a cross-sectional width smaller than a cross-sectional height in the distal portion.

18. A tissue removal tool for use with an endoscope, the tool comprising:
a loop formed by a piece of wire and movable between an open position and a closed position;
wherein the shape of the loop is defined in the open position by a proximal portion and a distal portion, the piece of wire having a cross-sectional height in the proximal portion unequal to a cross-sectional height in the distal portion;
wherein the proximal portion and the distal portion are separated by a transitional portion, wherein the loop is defined by a single twist that extends substantially along an elongate axis of the wire by at least 45 degrees on each side of the transitional portion; and
wherein the proximal portion comprises at least two collapse-resistant bends on at least one side of the loop.

* * * * *